(12) United States Patent
Davis et al.

(10) Patent No.: US 11,065,181 B2
(45) Date of Patent: Jul. 20, 2021

(54) SYRINGE-TO-SYRINGE COUPLER

(71) Applicant: NeoMed, Inc., Woodstock, GA (US)

(72) Inventors: Benjamin Martin Davis, Woodstock, GA (US); Aaron N. Ingram, Canton, GA (US); Mark M. Costello, County Mayo (IE); Tony Doherty, County Mayo (IE)

(73) Assignee: NeoMed, Inc., Woodstock, GA (US)

( * ) Notice: Subject to any disclaimer, the term of this patent is extended or adjusted under 35 U.S.C. 154(b) by 0 days.

(21) Appl. No.: 16/548,969

(22) Filed: Aug. 23, 2019

(65) Prior Publication Data

US 2020/0038291 A1 Feb. 6, 2020

Related U.S. Application Data

(63) Continuation of application No. 15/185,583, filed on Jun. 17, 2016, now Pat. No. 10,576,020.

(60) Provisional application No. 62/181,595, filed on Jun. 18, 2015.

(51) Int. Cl.
*A61J 1/20* (2006.01)
*A61M 39/10* (2006.01)

(52) U.S. Cl.
CPC .......... *A61J 1/2096* (2013.01); *A61J 1/2048* (2015.05); *A61J 1/2089* (2013.01); *A61J 1/2075* (2015.05); *A61M 2039/1088* (2013.01)

(58) Field of Classification Search
CPC ...... A61J 1/2096; A61J 1/2048; A61J 1/2089; A61J 1/2075; A61M 2039/1088
See application file for complete search history.

(56) References Cited

U.S. PATENT DOCUMENTS

| | | | | | |
|---|---|---|---|---|---|
| 2,477,598 | A | ‡ | 8/1949 | Hain | G01N 33/26 366/33 |
| 3,473,833 | A | ‡ | 10/1969 | Bremer | B29C 65/48 285/28 |
| 3,572,337 | A | ‡ | 3/1971 | Schunk | A61J 7/0053 604/77 |
| 4,046,145 | A | ‡ | 9/1977 | Choksi | A61J 1/2096 604/40 |

(Continued)

FOREIGN PATENT DOCUMENTS

CA 2 548 976 A1 12/2007
DE 7740288 U1 12/1977

(Continued)

OTHER PUBLICATIONS

Invitation to Pay Additional Fees for PCT/US2017/019021; Jun. 6, 2017; 12 pgs.‡

(Continued)

*Primary Examiner* — Nicolas A Arnett
(74) *Attorney, Agent, or Firm* — Dority & Manning, P.A.

(57) ABSTRACT

A syringe-to-syringe coupling for facilitating the transfer of fluids or medications from a first syringe to a second syringe. In example embodiments, the coupling includes a centrally-positioned hub extending from a first end to a second end, and a fluid delivery conduit provided within the hub and extending between the first and second ends. In example forms, each end of the hub includes a male tip.

14 Claims, 25 Drawing Sheets

(56) References Cited

U.S. PATENT DOCUMENTS

| | | | | |
|---|---|---|---|---|
| 4,685,173 A ‡ | 8/1987 | Pavur | | B60R 16/0222 16/2.2 |
| 4,743,229 A ‡ | 5/1988 | Chu | | A61J 1/2096 604/82 |
| 4,842,592 A ‡ | 6/1989 | Caggiani | | A61M 39/12 285/33 |
| D303,710 S ‡ | 9/1989 | Neill | | D24/23 |
| D327,318 S ‡ | 6/1992 | Dudar | | D24/11 |
| 5,224,937 A ‡ | 7/1993 | van der Heiden | | A61J 1/2089 604/19 |
| 5,405,339 A ‡ | 4/1995 | Kohnen | | A61M 39/12 285/23 |
| D395,502 S ‡ | 6/1998 | Deily | | D24/11 |
| D398,060 S ‡ | 9/1998 | Brown | | D24/16 |
| 5,957,166 A ‡ | 9/1999 | Safabash | | B01F 11/0082 141/10 |
| D435,652 S ‡ | 12/2000 | Nazarifar | | D23/26 |
| 6,270,519 B1 ‡ | 8/2001 | Botts | | A61J 7/0046 215/11 |
| D473,647 S ‡ | 4/2003 | Francavilla | | D24/12 |
| 6,592,251 B2 ‡ | 7/2003 | Edwards | | B01F 5/0685 366/13 |
| 6,726,672 B1 ‡ | 4/2004 | Hanly | | A61J 1/10 215/24 |
| D534,796 S ‡ | 1/2007 | Falkenburg | | D23/26 |
| 7,172,085 B2 | 2/2007 | Beaudette | | |
| 7,503,905 B2 ‡ | 3/2009 | Jessop | | A61C 9/0026 604/12 |
| 7,523,967 B2 ‡ | 4/2009 | Steppe | | A61M 39/10 285/40 |
| 7,594,681 B2 ‡ | 9/2009 | DeCarlo | | A61M 39/10 285/29 |
| 7,666,170 B2 ‡ | 2/2010 | Guala | | A61M 39/10 604/24 |
| 7,740,288 B2 ‡ | 6/2010 | Mantell | | A61M 13/003 285/33 |
| 7,766,919 B2 ‡ | 8/2010 | Delmotte | | A61B 17/8816 606/92 |
| 7,811,278 B2 ‡ | 10/2010 | Knipple, Jr. | | A61M 16/0816 604/53 |
| 7,857,284 B2 ‡ | 12/2010 | Kimball | | A61M 39/045 251/14 |
| 7,985,205 B2 ‡ | 7/2011 | Adams | | A61J 15/0015 604/17 |
| D644,618 S ‡ | 9/2011 | Morihira | | D13/19 |
| 8,016,795 B2 ‡ | 9/2011 | Barrelle | | A61J 7/0053 604/18 |
| 8,109,902 B2 ‡ | 2/2012 | Middleton | | A61J 1/2096 604/41 |
| 8,152,790 B2 ‡ | 4/2012 | Lopez | | A61M 39/26 604/53 |
| 8,267,571 B2 * | 9/2012 | Johansson | | B01F 13/0023 366/139 |
| 8,303,571 B2 ‡ | 11/2012 | Kraushaar | | A61M 39/105 604/53 |
| 8,328,768 B2 ‡ | 12/2012 | Quigley | | A61M 1/367 604/16 |
| 8,398,607 B2 ‡ | 3/2013 | Fangrow, Jr. | | A61M 39/10 251/14 |
| 8,479,370 B2 ‡ | 7/2013 | Grant | | A61M 39/10 29/525 |
| 8,529,524 B2 ‡ | 9/2013 | Newton | | A61M 39/045 604/24 |
| D691,261 S ‡ | 10/2013 | Kawamura | | D24/13 |
| 8,551,068 B2 ‡ | 10/2013 | Kyle | | A61J 1/2096 604/41 |
| 8,613,738 B2 ‡ | 12/2013 | Mantell | | A61M 13/003 604/53 |
| 8,641,685 B2 ‡ | 2/2014 | Mansour | | A61M 39/1011 604/25 |
| 8,679,090 B2 ‡ | 3/2014 | Anderson | | A61M 39/26 604/53 |
| D712,025 S ‡ | 8/2014 | Kawamura | | D24/11 |
| D714,935 S ‡ | 10/2014 | Nishioka | | |
| 8,852,167 B2 ‡ | 10/2014 | Trombley, III | | A61M 39/10 604/53 |
| 8,870,834 B2 ‡ | 10/2014 | Milijasevic | | A61M 5/16877 604/24 |
| D716,636 S ‡ | 11/2014 | McDonald | | D8/354 |
| D717,948 S ‡ | 11/2014 | Strong | | D24/13 |
| 9,017,295 B2 ‡ | 4/2015 | Pan | | A61M 39/10 604/24 |
| 9,033,938 B2 ‡ | 5/2015 | Milijasevic | | A61M 5/16877 604/24 |
| D731,065 S ‡ | 6/2015 | Winter | | D24/1 |
| 9,073,021 B2 ‡ | 7/2015 | Nakamura | | A61J 1/20 |
| 9,078,809 B2 * | 7/2015 | Bochenko | | A61J 1/2062 |
| D736,914 S ‡ | 8/2015 | Schultz | | D24/12 |
| D736,915 S ‡ | 8/2015 | Schultz | | D24/12 |
| D737,962 S ‡ | 9/2015 | Schultz | | D24/12 |
| 9,126,029 B2 * | 9/2015 | Fangrow | | A61M 39/10 |
| 9,149,623 B1 * | 10/2015 | Colman | | A61B 5/097 |
| 9,289,587 B2 * | 3/2016 | Colman | | F16L 37/244 |
| D756,200 S ‡ | 5/2016 | McDonald | | D8/354 |
| 9,427,715 B2 * | 8/2016 | Palazzolo | | B01F 5/0685 |
| 9,433,562 B2 ‡ | 9/2016 | Ingram | | A61J 15/00 |
| 10,576,020 B2 * | 3/2020 | Davis | | A61J 1/2089 |
| 10,624,816 B2 | 4/2020 | Davis et al. | | |
| 2003/0132185 A1 | 7/2003 | Beaudette | | |
| 2005/0209555 A1 ‡ | 9/2005 | Middleton | | A61J 1/2096 604/82 |
| 2006/0217679 A1 ‡ | 9/2006 | Hanly | | A61J 1/10 604/40 |
| 2007/0021775 A1 | 2/2007 | Niedospial, Jr. et al. | | |
| 2007/0076401 A1 ‡ | 4/2007 | Carrez | | A61M 39/10 361/81 |
| 2008/0183153 A1 ‡ | 7/2008 | Enns | | A61M 39/10 604/53 |
| 2008/0312640 A1 ‡ | 12/2008 | Grant | | A61M 39/10 604/53 |
| 2010/0022951 A1 ‡ | 1/2010 | Ferrera | | A61M 39/0613 604/10 |
| 2010/0087705 A1 ‡ | 4/2010 | Byers | | A61B 1/00128 600/10 |
| 2013/0098861 A1 | 4/2013 | Lair et al. | | |
| 2014/0020788 A1 ‡ | 1/2014 | Kyle | | A61J 1/2096 141/18 |
| 2014/0246616 A1 ‡ | 9/2014 | Fangrow | | A61M 39/18 251/14 |
| 2014/0276466 A1 ‡ | 9/2014 | Yeh | | A61M 39/26 604/25 |
| 2014/0276651 A1 ‡ | 9/2014 | Schultz | | A61M 39/165 604/53 |
| 2014/0323995 A1 ‡ | 10/2014 | Clauson | | A61F 9/0017 604/29 |
| 2015/0238747 A1 ‡ | 8/2015 | Russo | | A61M 39/1011 604/53 |
| 2016/0001056 A1 ‡ | 1/2016 | Nelson | | A61M 39/045 604/24 |
| 2016/0030293 A1 ‡ | 2/2016 | Dorsey | | A61J 15/0096 604/50 |
| 2016/0067147 A1 ‡ | 3/2016 | Davis | | B65D 47/141 220/30 |
| 2016/0067422 A1 ‡ | 3/2016 | Davis | | A61M 5/3202 604/19 |
| 2016/0067471 A1 ‡ | 3/2016 | Ingram | | A61M 39/10 604/53 |
| 2016/0084414 A1 ‡ | 3/2016 | Groepper | | A61M 39/10 285/80 |
| 2016/0143815 A1 ‡ | 5/2016 | Koelper | | A61J 15/0026 604/53 |
| 2016/0159635 A1 ‡ | 6/2016 | Davis | | B67D 3/0041 141/36 |
| 2016/0206516 A1 ‡ | 7/2016 | Kunishige | | A61J 15/0026 |
| 2016/0206845 A1 ‡ | 7/2016 | Colman | | A61M 16/0816 |
| 2016/0208971 A1 | 7/2016 | Lewis et al. | | |
| 2016/0317393 A1 ‡ | 11/2016 | Davis | | A61M 39/12 |

(56) References Cited

U.S. PATENT DOCUMENTS

| | | | | |
|---|---|---|---|---|
| 2016/0367439 | A1 ‡ | 12/2016 | Davis | A61J 1/2096 |
| 2017/0045170 | A1 | 2/2017 | Lewis et al. | |
| 2017/0239141 | A1 ‡ | 8/2017 | Davis | B65D 43/163 |

FOREIGN PATENT DOCUMENTS

| | | | | |
|---|---|---|---|---|
| DE | 7740288 U1 ‡ | 12/1977 | | |
| DE | 8613738 | 7/1986 | | |
| DE | 8613738 U1 ‡ | 7/1986 | | H01T 13/04 |
| DE | 20302788 U1 | 6/2004 | | |
| DE | 20302788 U1 ‡ | 6/2004 | | A61M 39/1011 |
| DE | 102005030510 A1 | 1/2007 | | |
| DE | 102005030510 A1 ‡ | 1/2007 | | B01F 13/0023 |
| DE | 731065 | 6/2015 | | |
| EP | 0960616 A2 ‡ | 12/1999 | | B65D 51/002 |
| EP | 0960616 A2 | 12/1999 | | |
| EP | 2269685 A2 | 1/2011 | | |
| EP | 2269685 A2 ‡ | 1/2011 | | A61M 39/26 |
| EP | 3042691 A1 | 7/2016 | | |
| EP | 3042691 A1 ‡ | 7/2016 | | A61J 15/00 |
| FR | 2930428 A1 | 10/2009 | | |
| FR | 2930428 A1 ‡ | 10/2009 | | A61J 7/0053 |
| JP | 4743229 B2 ‡ | 8/2011 | | |
| JP | 4743229 B2 | 8/2011 | | |
| WO | WO 9200717 A1 | 1/1992 | | |
| WO | WO-9200717 A1 ‡ | 1/1992 | | A61J 7/0053 |
| WO | WO 9932155 A2 | 7/1999 | | |
| WO | WO-9932155 A2 ‡ | 7/1999 | | A61B 17/00491 |
| WO | WO 2005/065767 A2 | 7/2005 | | |
| WO | WO-2005065767 A2 ‡ | 7/2005 | | A61M 5/3134 |
| WO | WO 2008/128074 A2 | 10/2008 | | |
| WO | WO-2008128074 ‡ | 10/2008 | | |
| WO | WO 2009/090627 A1 | 7/2009 | | |
| WO | WO-2009090627 A1 ‡ | 7/2009 | | A61J 1/2096 |
| WO | WO 2012/024370 A1 | 2/2012 | | |
| WO | WO-2012024370 ‡ | 2/2012 | | |
| WO | WO 2013/081699 A2 | 6/2013 | | |
| WO | WO-2013081699 A2 ‡ | 6/2013 | | B65D 83/0005 |
| WO | WO 2014/049097 A1 | 4/2014 | | |
| WO | WO-2014049097 ‡ | 4/2014 | | |
| WO | WO 2015/034045 A1 | 3/2015 | | |
| WO | WO-2015034045 A1 ‡ | 3/2015 | | A61J 15/0026 |
| WO | WO 2016/040126 A1 | 3/2016 | | |
| WO | WO-2016040126 ‡ | 3/2016 | | |
| WO | WO 2016/089869 A1 | 6/2016 | | |
| WO | WO-2016089869 A1 ‡ | 6/2016 | | A61J 15/0026 |
| WO | WO 2016/154304 A1 | 9/2016 | | |
| WO | WO 2018/022631 A1 | 2/2018 | | |
| WO | WO-2018022631 ‡ | 2/2018 | | |

OTHER PUBLICATIONS

International Search Report & Written Opinion for PCT/US2016/038051; dated Sep. 2, 2016; 13 pgs.‡

International Search Report & Written Opinion for PCT/US2016/023771; dated Jun. 27, 2016; 17 pgs.‡

Non Sterile Luer Lock to Oral Slip Adapter; Health Care Logistics, Inc.; 1 pg; date unknown.‡

Oral Slip to Oral Slip Adapter; Health Care Logistics Inc.; 1 pg; date unknown.‡

New Tube Feeding Connectors Webinar PowerPoint Presention; www.oley.org; 24 pgs; Jun. 24, 2014.‡

New ISO Tubing Connector Standards: A Follow-Up to the Sentinel Event Alert Webinar PowerPoint Presention; www.jointcommission.org; 50 pgs; Dec. 3, 2014.‡

International Search Report & Written Opinion for PCT/US2016/042514; dated Nov. 10, 2016; 12 pgs.‡

Baxa (Baxter) Rapidfill Connector; date unknown; 1 pg.‡

Vygon Fluid Dispensing Connector; 1 pg; date unknown.‡

Covidien ENFit Coupling; Mar. 2014; 1 pg.‡

Alternative Syringes Low Displacement Option PowerPoint Presention; Presented by Rork Swisher of Covidien; ISO 80369 Series Meeting; Berlin Germany; 11 pgs; Mar. 19, 2014.pgs.‡

Sterile Luer Lock to Oral Slip Adapter; Health Care Logistics, Inc.; 1 pg; date unknown.‡

Specialty Medical Products Coupling (Item Code SMP-SCFF); Apr. 10, 2014; 1 pg.‡

International Search Report & Written Opinion for PCT/US2017/019021; dated Sep. 22, 2017; 20 pgs.‡

Alternative Syringes Low Displacement Option PowerPoint Presentation; Presented by Rork Swisher of Covidien; ISO 80369 Series Meeting; Berlin Germany; 11 pgs; Mar. 19, 2014.

International Search Report & Written Opinion for PCT/US2016/042514; dated Nov. 10, 2015; 12 pgs.

New ISO Tubing Connector Standards: A Follow-Up to the Sentinel Event Alert Webinar PowerPoint Presentation; www.ointcommission.org; 50 pgs; Dec. 3, 2014.

New Tube Feeding Connectors Webinar PowerPoint Presentation; www.oley.org; 24 pgs; Jun. 24, 2014.

Tulip Medical GEMS Syringe Locks & Single-Use Anaerobic Transfers; 1 pg; date unknown.

\* cited by examiner
‡ imported from a related application

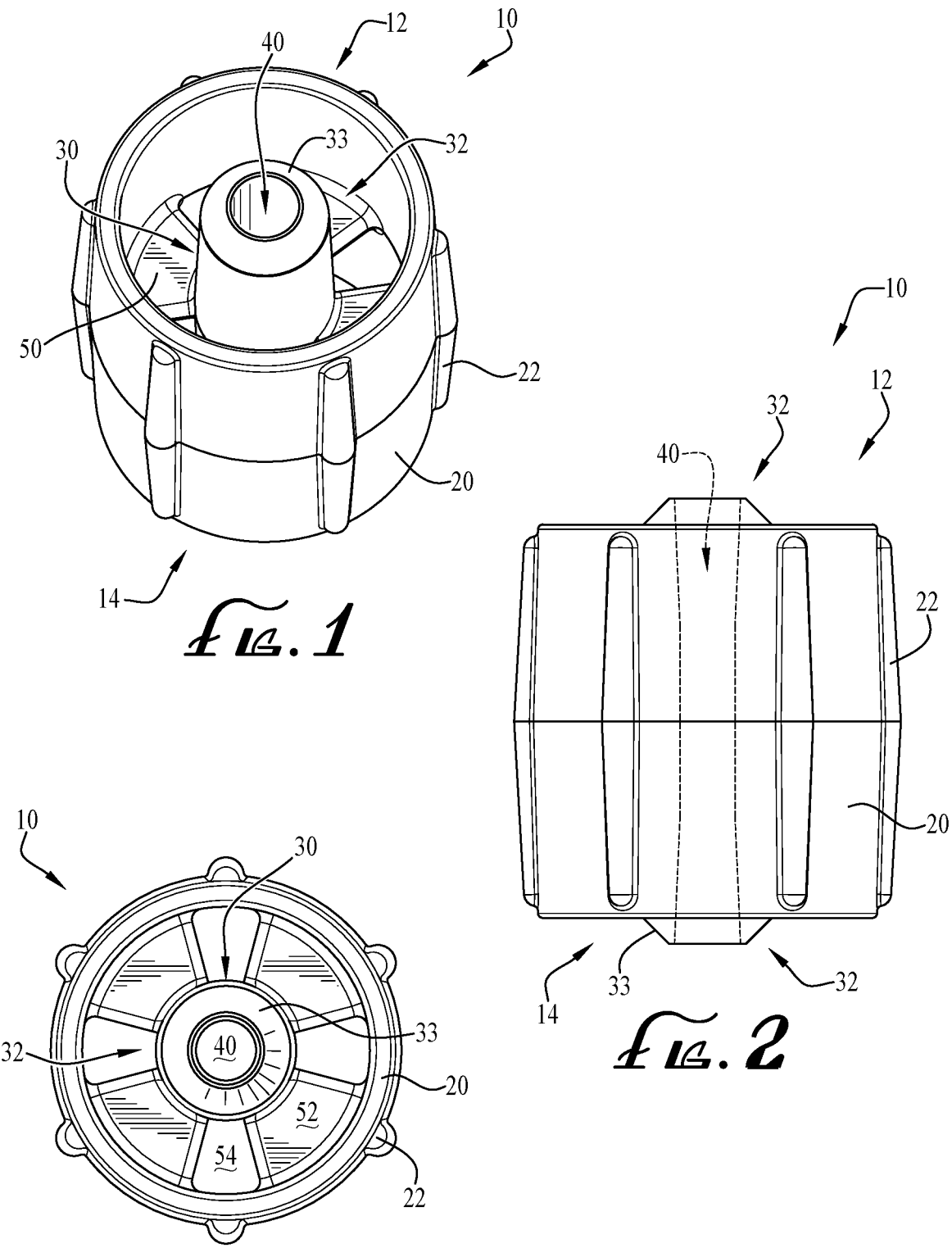

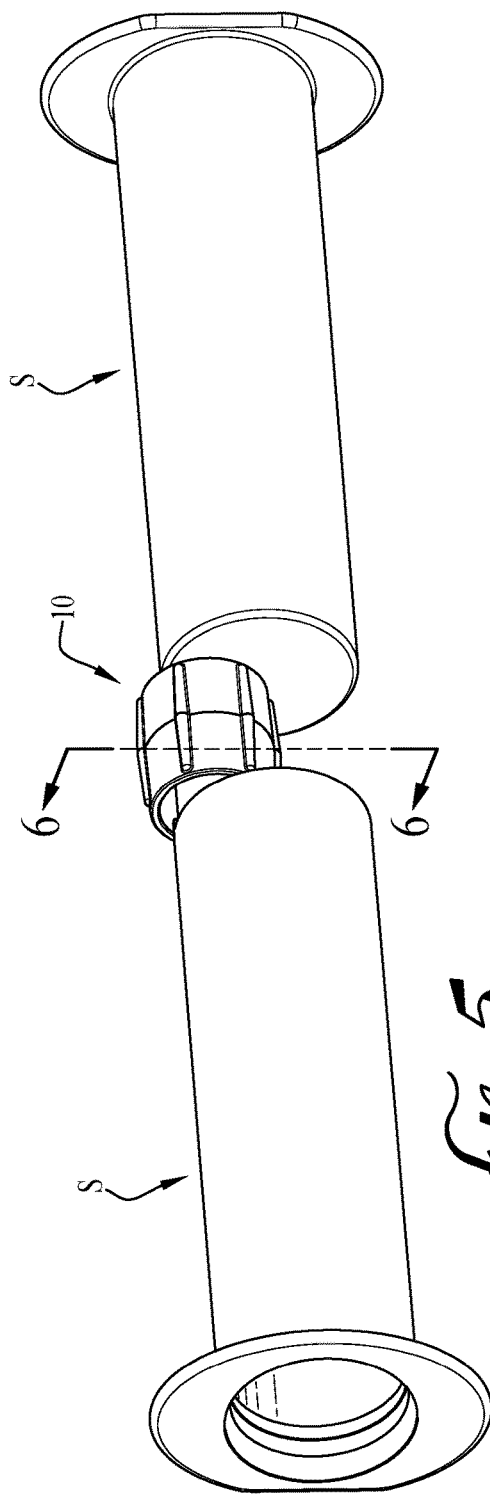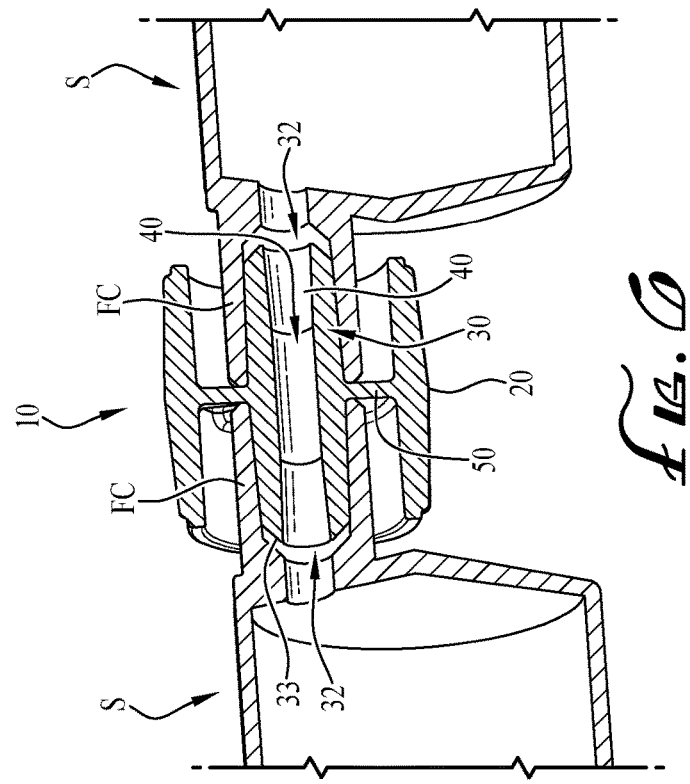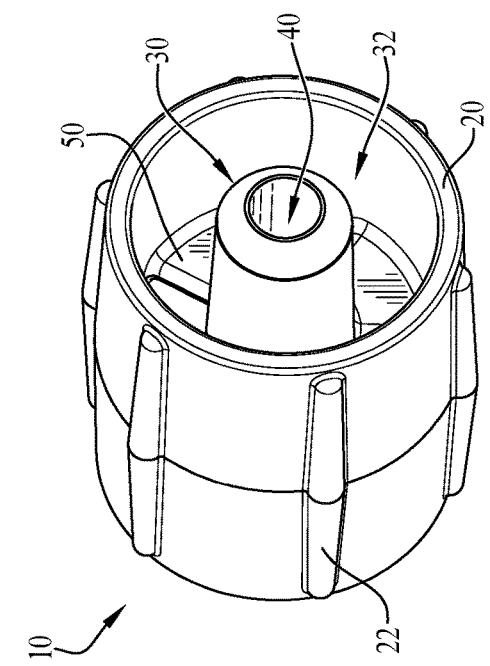

SYRINGE-TO-SYRINGE COUPLER

CROSS-REFERENCE TO RELATED APPLICATION

This application claims the priority benefit of U.S. Provisional Patent Application Ser. No. 62/181,595 filed Jun. 18, 2015, the entirety of which is hereby incorporated by reference herein.

TECHNICAL FIELD

The present invention relates generally to the field of containment, storage, delivery and transfer of fluids, particularly in the medical and pharmaceutical fields, and more particularly to a coupler for devices used in the transfer of medical or nutritional fluids.

BACKGROUND

Various fluids such as medications and nutritional fluids are delivered to human or animal patients by dispensing from a syringe. For example, the enteral delivery of formula, breast milk, nutritional supplements, medication and the like to neonatal infants may utilize syringes for manual delivery or automated delivery using a syringe pump.

In some cases, it is desirable to transfer the fluids between syringes, for example, for mixing of fluids, when smaller doses are desired, to consolidate fluids from multiple containers, or for other various purposes. Syringes conforming to the new ENFit design standard (ISO 80369-3) may include nipple or tip couplings of differing format and larger dimension and volume or displacement than previous syringes.

Thus it can be seen that needs exist for improvements to couplers for transferring fluids between syringes. It is to the provision of an improved syringe-to-syringe coupler meeting these and other needs that the present invention is primarily directed.

SUMMARY

The present invention is directed to field of containment, storage, delivery and transfer of fluids, particularly in the medical and pharmaceutical fields, and more particularly to a coupler for devices used in the transfer of medical and nutritional fluids. In one aspect, the present invention relates to a coupling for transferring fluids between at least two ISO 80369-3 ENFit female connectors or compatible connectors including a male-male hub extending from a first end to a second end, and a fluid delivery conduit extending through the hub from the first end to the second end. In example forms, the ends of the male-male hub are at least partially tapered. In some example forms, the two ISO 80369-3 ENFit female connectors are formed with syringes.

In example embodiments, a body is provided and is outwardly offset from the male-male hub. In example forms, at least one connecting member extends between the male-male hub and the body for fixedly positioning the male-male hub relative to the body.

In another aspect, the present invention relates to a syringe-to-syringe coupling for facilitating the transfer of fluids or medications between two syringes, wherein each of the respective syringes include an ISO 80369-3 ENFit female connector having one or more lugs positioned about an outer periphery thereof. The coupling includes a centrally-positioned hub extending from a first end to a second end, a fluid delivery conduit provided within the hub and extending between the first and second ends, and a body outwardly offset from the hub.

In some example embodiments, the body is generally cylindrical in shape, and the hub is generally centrally-positioned with respect to the body. In example forms, at least one connecting member extends between an interior portion of the body and the hub for centrally positioning the hub relative to the body. In other example embodiments, the body includes two generally planar members oppositely-positioned and outwardly offset from the hub. In example forms, at least one connecting member fixedly connects the centrally-positioned hub to the oppositely-positioned planar members.

In another aspect, the present invention relates to a coupling for facilitating the transfer of fluids or medications including a centrally-positioned hub extending from a first end to a second end, a fluid delivery conduit provided within the hub and extending between the first and second ends, a body outwardly offset from the hub, at least one connecting member connecting the hub with the body, and at least one engagement member for providing coupling engagement with a syringe In some example embodiments, the at least one engagement member is configured for removable coupling engagement with the syringe. According to another example embodiment, the at least one engagement member is configured for permanent coupling engagement with the syringe. In another example embodiment, one of the first or second ends of the hub is in the form of a luer connector for connection with a tube set of a syringe fill pump, and wherein the other of the ends is in the form of an ENFit connector for connection with an ENfit female connector of a syringe.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments, and are not restrictive of the invention, as claimed.

BRIEF DESCRIPTION OF THE DRAWINGS

FIG. 1 is a perspective view of a syringe-to-syringe coupler according to an example embodiment of the present invention.

FIG. 2 shows a side view of the syringe-to-syringe coupler of FIG. 1.

FIG. 3 shows a top view of the syringe-to-syringe coupler of FIG. 1.

FIG. 4 shows a perspective view of the syringe-to-syringe coupler of FIG. 1.

FIG. 5 shows two syringes coupled to the syringe-to-syringe coupler of FIG. 1.

FIG. 6 shows a detailed sectional view of the syringe-to-syringe coupler and syringes of FIG. 5.

DETAILED DESCRIPTION OF EXAMPLE EMBODIMENTS

Figure 7:
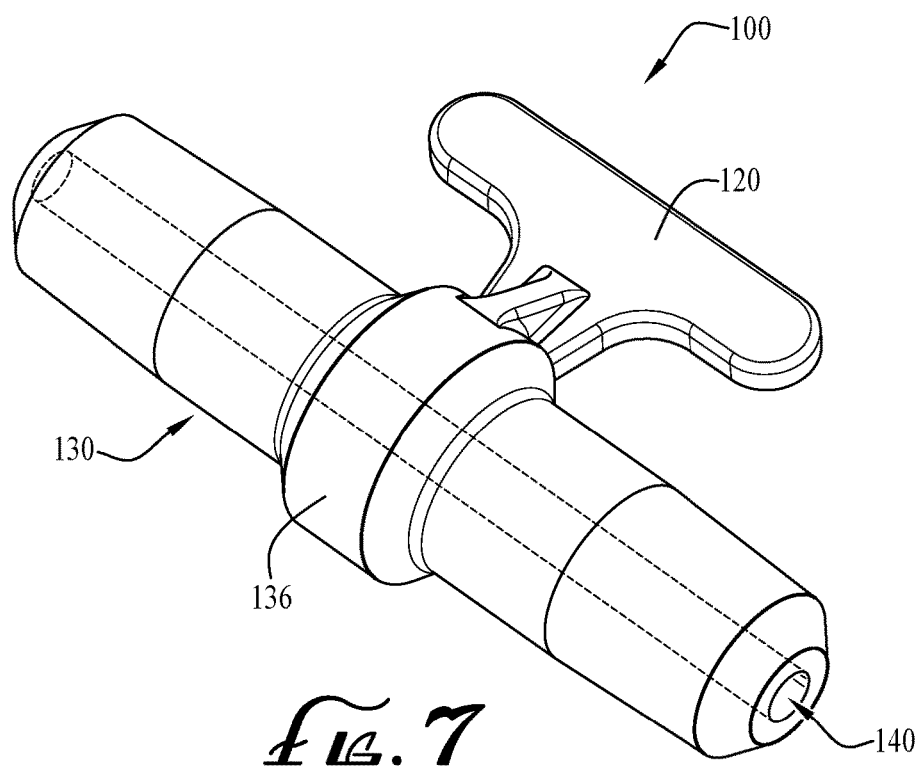
FIG. 7 is a perspective view of a syringe-to-syringe coupler according to another example embodiment of the present invention.

The present invention may be understood more readily by reference to the following detailed description taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

With reference now to the drawing figures, wherein like reference numbers represent corresponding parts throughout the several views, FIGS. 1-42 show a plurality of syringe-to-syringe couplers according to example embodiments of the present invention. Generally, the coupler generally includes a central fluid transfer member or hub extending from a first male tip configured to receive a first syringe S to a second male tip configured to receive a second syringe S. Preferably the hub includes a fluid transfer conduit or lumen extending between the male tips, thereby providing for fluid communication between the first and second syringes S.

In example forms, the syringe S includes a female connector FC in the form of an ENFit female connector according to the global design standard ISO 80369-1 (see FIGS. 5-6). Generally, the female connector FC comprises a pair of thread lugs or ribs R extending along a portion of the periphery of the connector. In some example embodiments, the coupler engages each syringe by a non-threaded, slip-fit connection such that the female connector FC (or an internal surface thereof) engages with a male tip of the coupler. According to other example embodiments, a substantially threaded outer collar member or engagement member is provided for engagement with the ribs of the female coupler, thereby providing secure and removable attachment of the coupling with the female connector FC of the syringe S. Alternatively, one or more clips, engagement ribs or other engagement members are provided with the coupling for removable or permanent attachment with the female connector FC (and ribs R thereof) of the syringe S.

Furthermore, at least one of the coupling embodiments shown in the figures is preferably capable of being adapted for connection with a syringe fill pump, for example, for connection with a tube set of the pump at one of the ends and for connection with a female connector FC at the other end. As will be described below, example embodiments of the present invention provide for a plurality of configurations to facilitate the transfer of fluids between syringes. For example, one or both ends of the coupling can be configured for a slip-fit connection (e.g., frictional engagement), or can additionally include a threaded collar, clips, or other engagement members for providing removable or permanent engagement with the female connector FC and ribs R thereof. Thus, in light of the plurality of embodiments described herein and as shown in FIGS. 1-42, any one of the connectors (or ends of the coupling) as described herein can be adapted for use with another one of any of the connectors (or ends of the coupling) as described herein.

FIGS. 1-6 show a syringe-to-syringe coupler 10 according to an example embodiment of the present invention. The coupler 10 is configured to engage two syringes with a removable slip-fit coupling or connection. As depicted, the coupler 10 comprises a central hub 30 (e.g., male-male hub) with two male tips 32 that is generally centrally positioned within an outer body 20 of the coupling 10. In example forms, the central hub 30 comprises a first end 12 having a first male tip 32 and a second end 14 having a second male tip 32. In example embodiments, the extension of the central hub 30 is generally linear; however, in alternate example embodiments, the extension of the central hub 30 can be generally non-linear, arcuate, or otherwise extend along a desired path between the first and second ends 12, 14.

The fluid conduit 40 is generally axially positioned within the hub 30 and generally extends entirely therethrough (e.g., extending between the first and second ends through the first and second male tips 32). In example embodiments, the opening 40 is cylindrical in shape and is generally sized to ensure accuracy of the quantity of fluid being transferred between the syringes S. In example embodiments, the male tips 32 can be at least partially tapered (as will be described in greater detail below) to provide for sufficiently frictional engagement with the female connector FC.

The outer body 20 is generally cylindrical in shape and centrally positioned concentrically around the hub 30. In the depicted example embodiment, the outer body 20 is open at each end and the body's outer surface includes ribs 22 to facilitate gripping or twisting of the coupler 10. In alternate embodiments, the body 20 can employ indents or other texturing to aid in gripping or twisting, for example, to benefit a user or operator in grasping or gripping the body 20 during attachment or detachment of the coupler 10 to/from one or more syringes S.

In example embodiments, the ends of the hub 30 extend beyond the ends of the outer body 20, for example, such that at least a portion of the male tips 32 protrude beyond the ends of the outer body (see FIG. 2). In alternative embodiments, the outer body 20 can be longer than the hub 30. For example, according to some example forms, when it is generally only the slip-fit connection providing for the engagement between the female connector FC and the male tip 232 and portion of the hub 30 (as depicted in FIGS. 1-8), the male tips 232 and the outer periphery of the hub 30 are preferably shaped for substantial frictional, slip-fit coupling engagement with the female connector FC.

In example embodiments, at least one connecting member or generally central transverse flange 50 retains the hub 30 concentrically or coaxially within the outer cylindrical housing 20 of the coupling 10. As shown in FIG. 3, the flange 50 can include a radial array of spaced-apart ribs or wedge-shaped fins 52 and openings or passages 54. In the depicted embodiment, the coupling 10 comprises four fins 52 and four passages 54. Thus, in example forms, each of the fins 52 fixes together the outer body 20 and the hub 30. And, the passages 54 provide for fluid drainage and/or airflow ventilation through the coupling (and external of the hub 30), for example, to prevent fluids or other matter from remaining stagnant within the coupling and potentially contaminating the coupling 10. U.S. Non-Provisional patent application Ser. No. 14/844,956 is incorporated herein by reference and discloses alternative connecting members providing ventilation.

To use the coupler 10, as shown in FIG. 5-6, the female connector FC of the first syringe S is slip-fitted over the first male tip 32 of the hub 30 (e.g., providing frictional engagement therebetween), and the female connector FC of the second syringe S is similarly attached to the second male tip 32 (e.g., providing frictional engagement therebetween). Preferably, the lumen 40 provides a passageway or conduit for transferring fluid between the syringes S. In example embodiments, the slip-fit connection between the male tips 32 and the female connectors FC of the syringes S is preferably a friction fit connection, for example, such that the frictional engagement provided between the outer periphery of the hub 30 and the interior surface of the female connector FC causes sufficient interference to remain snug and connected with the female connector FC of the syringe S. Preferably, a seal is provided by frictional engagement (e.g., preventing leaking) between the female connector FC and each male tip 32 and outer periphery of the hub 30.

In example forms, despite substantial frictional engagement, the coupler 10 can be easily disconnected from one or more of the female connectors FC when it is desired to do so (e.g., after fluid transfer between the syringes S is finished). According to some example forms, grasping and rotating the coupling 10 relative to the syringe S is effective in initiating disconnection of the coupling from the syringe S. According to example embodiments and as depicted in FIG. 6, the hub 30 of the connector 10 is preferably sized and shaped to provide a secure frictional fit with the internal surface of the female connector FC of the syringe S. In example embodiments, the male tips 32 can comprise a chamfered surface or end 33, which as shown in FIG. 6, is generally angled similarly with respect to an internal surface of the female connector FC and generally offset therefrom. The size and shape of the lumen 40 can be configured as desired, for example, to provide the desired volume of dead space or priming space within at least a portion of the lumen, for example, to substantially eliminate any dosing inaccuracies. For example, as depicted in FIGS. 5-6, when transferring fluid between the two syringes S, the volume of fluid output from one of the syringes S is substantially equal to the volume of fluid input to the other one of the syringes S.

Figure 8:
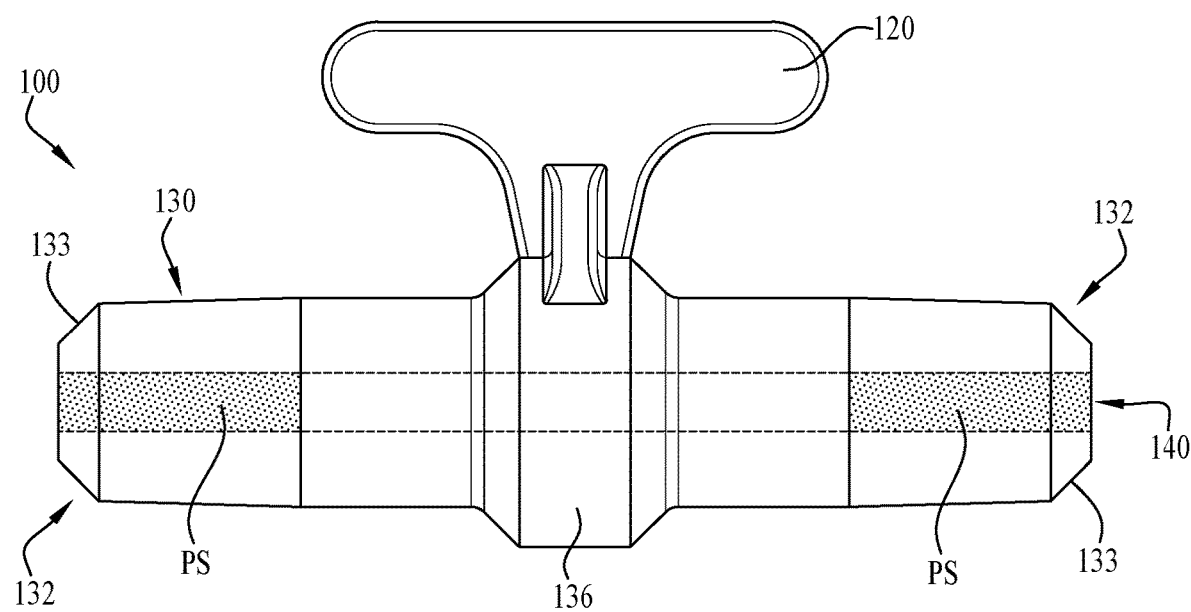
FIG. 8 shows a front view of the syringe-to-syringe coupler of FIG. 7.

FIGS. 7-8 show a syringe-to-syringe coupler 100 according to another example embodiment of the present invention. The coupler 100 is configured to engage two syringes S with a removable slip-fit coupling, for example, to facilitate the transfer of fluids between the two syringes S. In example embodiments, the coupler 100 generally comprises a hub 130 with two male tips 132 of the same size and shape of the previously described hub 30, and a lumen 140 generally axially extending through the entirety of the hub 130 between the two male tips 132. In the depicted embodiment, the coupler 100 includes a gripping handle 120 attached to a central portion of the hub 130. In example embodiments, the central portion of the hub 130 comprises a raised rib or protrusion 136, which generally extends entirely around the outer periphery of the hub 130. In alternative embodiments, the hub 130 can include a ring or other gripping attachment.

As depicted in FIG. 8, a portion of the lumen 140 of the male tips 132 preferably comprises a dead space or priming space PS within a contained volume of about 0.05 milliliters (ml). Preferably, the total dead space equals that of the hub fluid conduit 140 that is inserted into a syringe. In example forms, each male tip 132 generally comprises a priming space PS of between about 0.01 milliliters to about 0.20 milliliters, more preferably between about 0.04 milliliters to about 0.12 milliliters, and more preferably between about 0.04691 milliliters to about 0.09382 milliliters. During use of the coupler, the priming space or the fluid occupying the priming space should essentially prime the coupler the same way that another male connector would, for example, a male coupler of a syringe tip, other couplers, etc. In other words, the priming space in the coupler is configured such that the volume of the fluid delivered through the coupling (for transferring to another syringe, bottle, or other container, etc.) is the volume of the fluid filled within the syringe, bottle, or other container, etc., thereby eliminating any potential dosing inaccuracies through the transfer of fluids.

Figure 9:
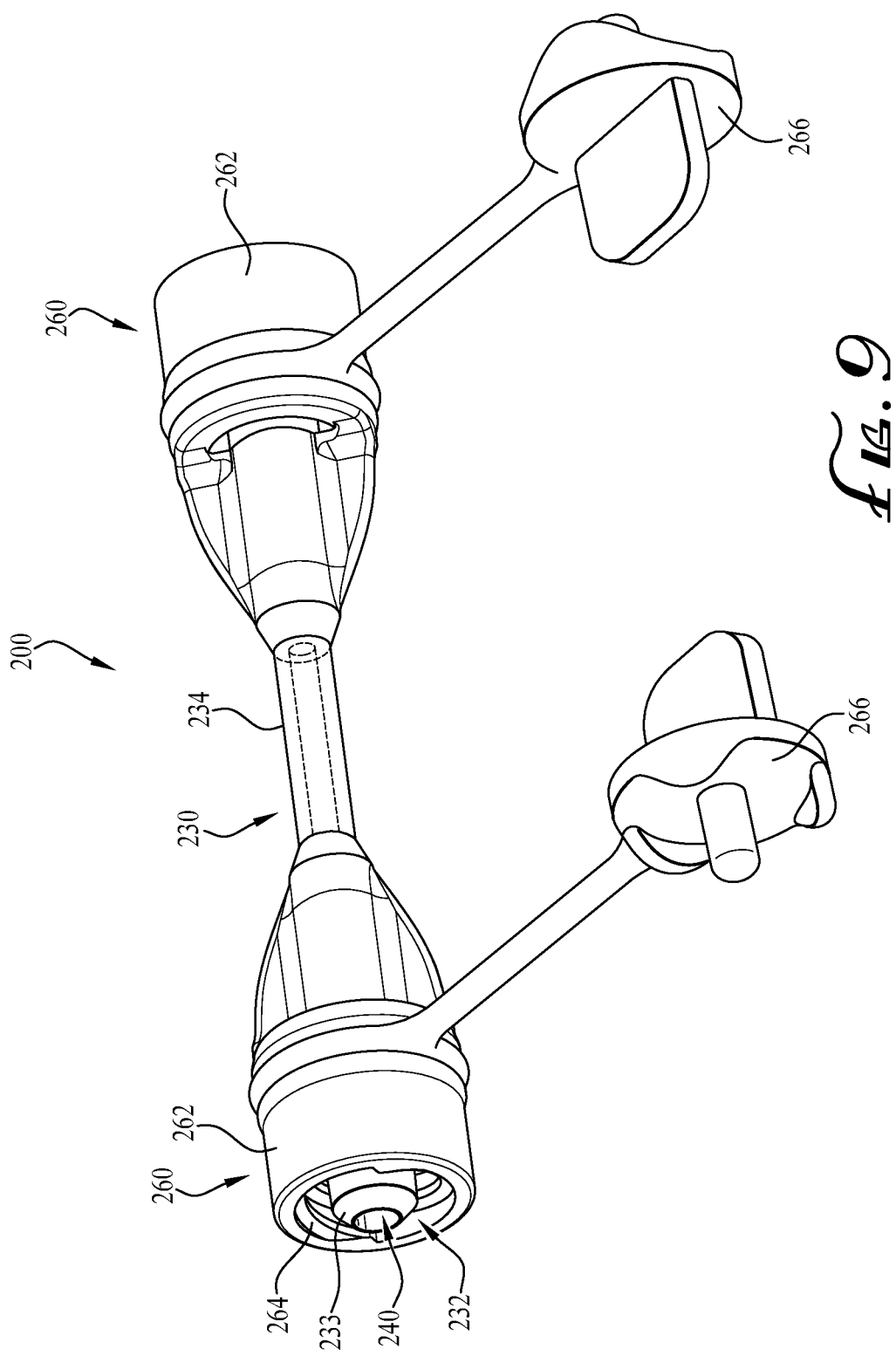
FIG. 9 is a perspective view of a syringe-to-syringe coupler according to another example embodiment of the present invention.

FIG. 9 shows a syringe-to-syringe coupler 200 according to another example embodiment of the present invention. In example embodiments, the coupler 200 is configured to removably engage two syringes S with threaded couplings. As depicted, the coupler comprises a hub 230 and a pair of engagement members or coupling elements 260. The hub 230 comprises an elongated tubular body 234 with two male coupling tips 232, for example, a first male tip 232 at a first end and a second male tip 232 at a second end. Generally, the male tips 232 are substantially similar to the male tips 32, 132 as describe above, for example, which comprises a chamfered surface formed on each of the ends. The tubular body 234 can be constructed of a rigid or flexible material. In alternate embodiments, the tubular body 234 of the hub 230 may be detachably connected to each male tip 232.

As similarly described above, an opening or fluid conduit 240 extends through the hub 230 from the first end to the second end (e.g., from the first male tip 232, through the tubular body 234, and to the second male tip 232). The coupling elements 260 are formed at each end of the hub 230, for example, wherein each coupling element 260 comprises a generally cylindrically shaped outer housing 262 surrounding the respective male tip 232 such that the inner sidewall of the outer housing is generally coaxially arranged with the male tip 232 thereby forming an annular space therebetween. The inner sidewall of the outer housing 262 includes screw threads 264 to provide for interengagement with the ribs R of the female connector FC of each respective syringe S. In example embodiments, the coupling elements 260 and the outer housings 262 thereof can be in the form of an outer collar member, for example, which comprises a cylindrical body comprising threads formed on an internal surface thereof to accommodate removable engagement with the female connector FC (and the ribs R thereof). To removably engage a syringe S with the respective coupling element 260, the female connector FC is inserted into the annular space between the male tip 232 and the outer housing 262 such that the ribs R are generally oriented to interengage with the threads 264 on the outer housing. Either the coupling 200 or the syringe S is rotated relative to the other to provide for removable engagement therebetween. In example embodiments, a tethered cap or plug 266 is optionally attached to one or both of the coupling elements 260 to allow closure of one or both of the ends of the fluid conduit as desired. In alternate embodiments other conventional mating fasteners such as are known to persons of ordinary skill in the art can be used, for example, those disclosed in U.S. Non-Provisional patent application Ser. No. 14/844,956, which is incorporated herein by reference.

Figure 10:
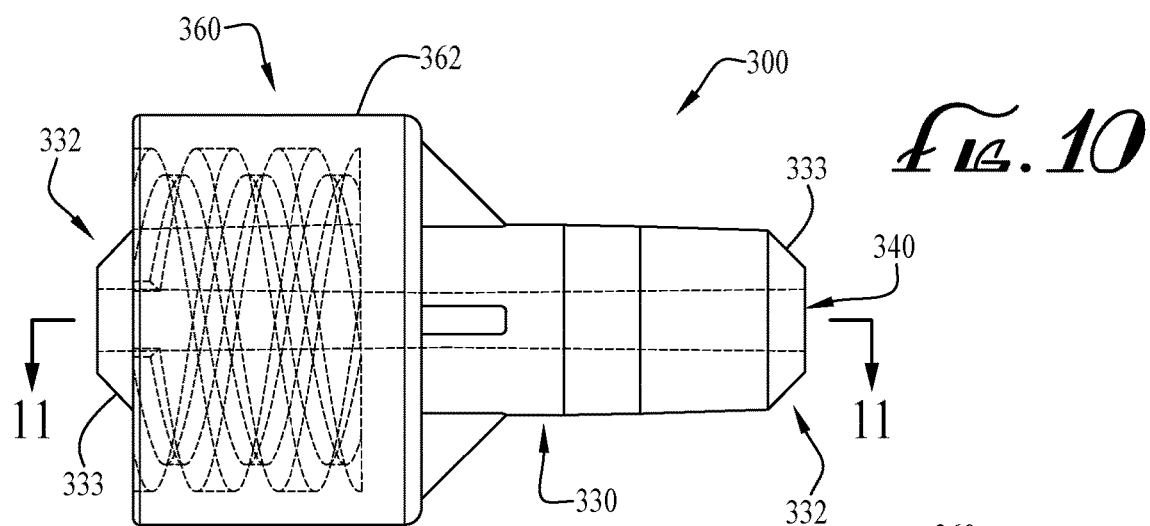
FIG. 10 is a side view of a syringe-to-syringe coupler according to another example embodiment of the present invention.
Figure 11:
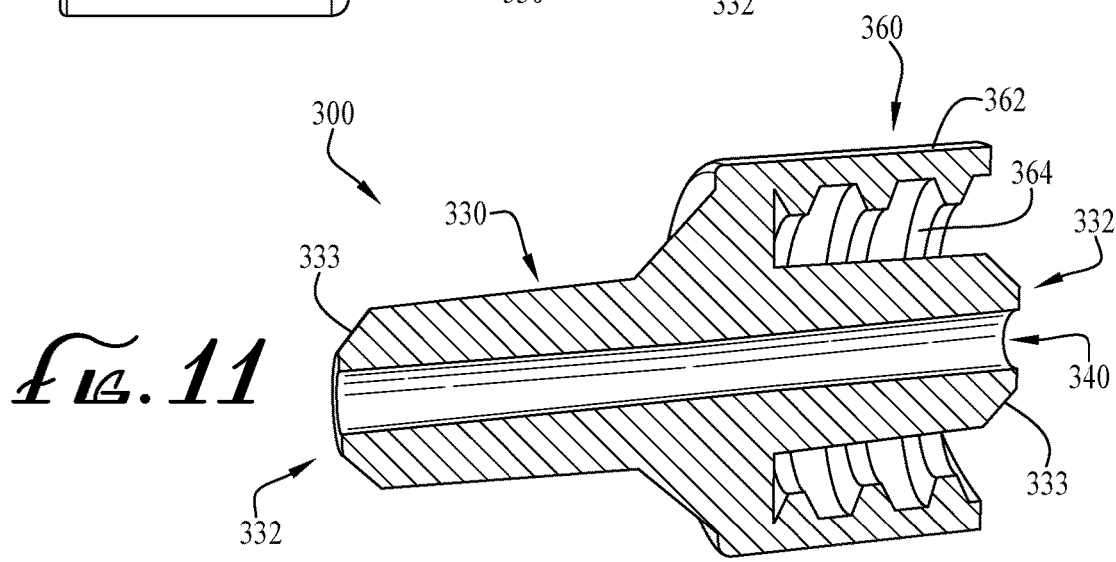
FIG. 11 shows a sectional view of the syringe-to-syringe coupler of FIG. 10 taken along line 11-11.
Figure 12:
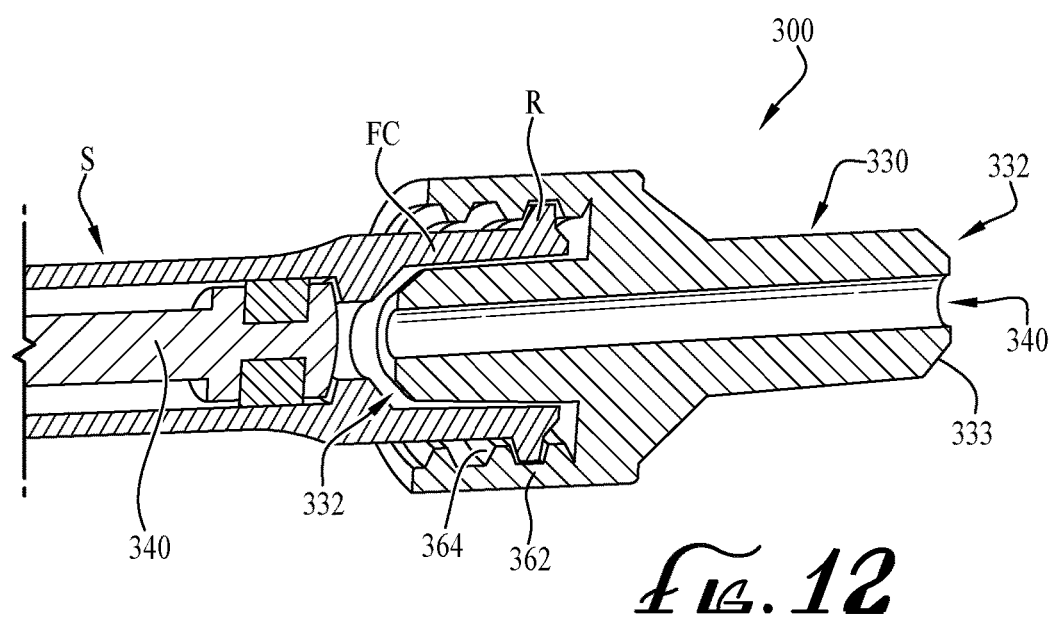
FIG. 12 shows a cross section view of the syringe-to-syringe coupler of FIG. 10 attached to a syringe.

FIGS. 10-12 show a syringe-to-syringe coupler 300 according to another example embodiment of the present invention. The coupler 300 is configured to removably engage a first syringe S with a slip-fit coupling and a second syringe with a threaded coupling. In example embodiments, the coupler 300 comprises a hub 330 and fluid conduit 340 of similar size and shape as the hub of previously described couplers 10, 100. The coupler 300 comprises an engagement member or coupling element 360, for example, an outer collar member, comprising a generally cylindrically shaped outer housing 362 generally beginning at a center or midpoint of the hub and extending toward one of the male tips 332. An inner surface of the outer housing 362 comprises a threaded portion 364 for providing interengagement with the female coupling FC (and ribs R thereof) of the syringe S. in example embodiments, the coupling element 360 is configured to be coupled to the female connector FC of the syringe S by configuring the ribs R of the female connector FC to interengage with the threads 364 of the outer housing 362, thereby axially moving one of the coupling 360 or female connector FC toward each other. To disengage the coupling element 360 from the female connector FC, the coupling element is generally unscrewed from the female connector. The second syringe (not shown) is slip fitted onto the second male tip 332.

Figure 13:
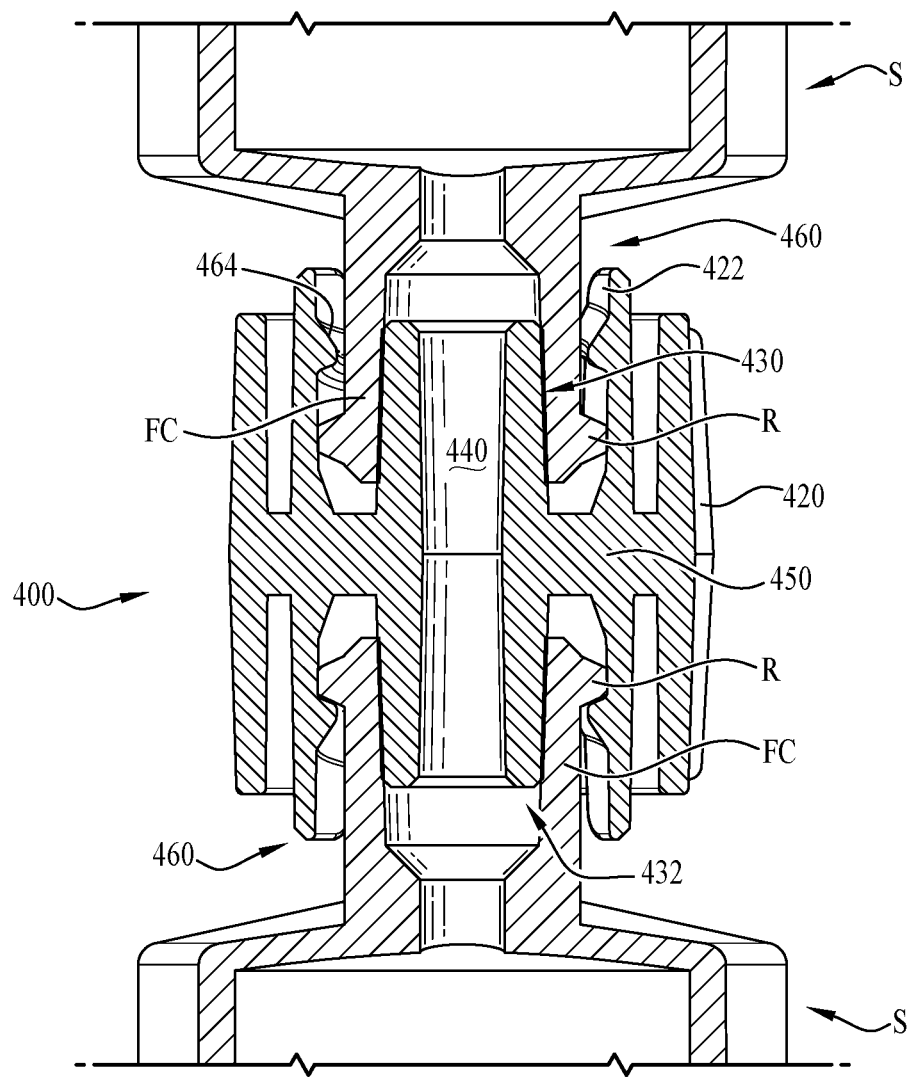
FIG. 13 is a detailed cross-sectional view of a syringe-to-syringe coupler coupled between two syringes according to another example embodiment of the present invention.
Figure 14:
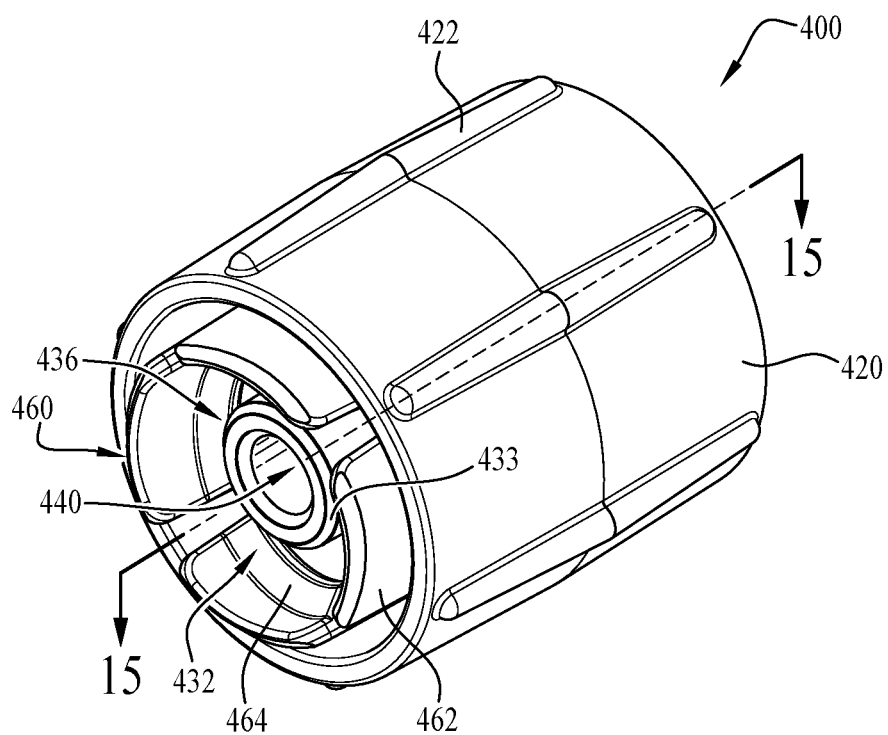
FIG. 14 shows a perspective view of the syringe-to-syringe coupler of FIG. 13.
Figure 15:
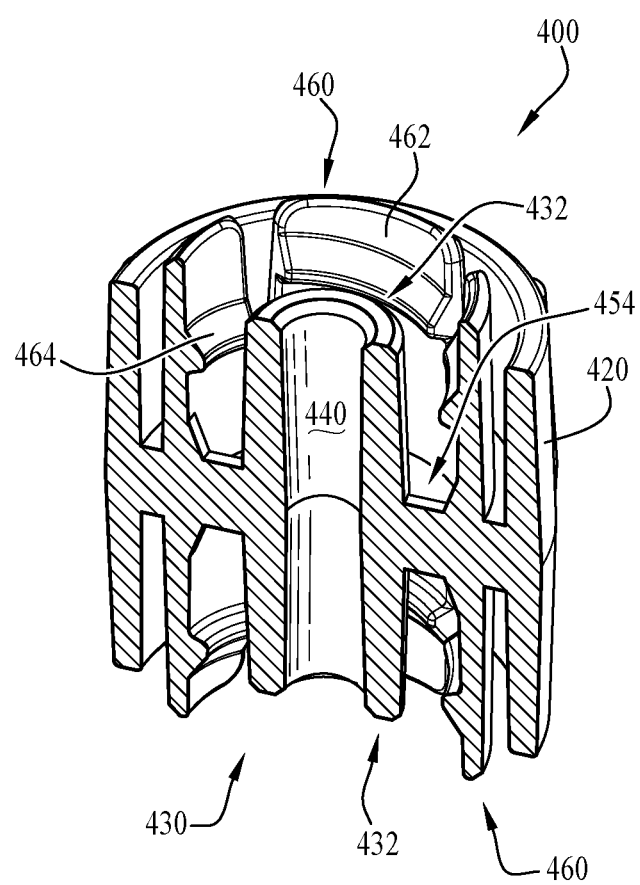
FIG. 15 shows a sectional view of the syringe-to-syringe coupler of FIG. 14 taken along line 15-15.

FIGS. 13-15 show a syringe-to-syringe coupler 400 according to another example embodiment of the present invention. The coupler 400 is configured to removably couple two syringes S together to facilitate the transfer of fluids therebetween. In example embodiments, the coupler 400 includes a hub 430 and fluid conduit 440 of similar size and shape as the previously described embodiment. The coupler 400 includes engagement members or coupling elements 460 provided at each end of the coupler 400 and generally surrounding the hub 430. In example embodiments, each coupling element 460 comprises four tab members or clips 462 that generally form a circular array at a distance from the hub 430 generally extending from a central portion or midpoint of the hub 430 toward one of the male tips 432. An internal portion or wall of at least one of the clips 462 includes a threaded portion 464. In the depicted embodiment, each of the four clips 462 includes at least a portion of a thread 464. In example forms, the female connector FC of each syringe S can be installed and removed by either pushing and pulling (without twisting) due to the snap connection provided by the split collar and the rib R, or by twisting on and off due to the thread 464 on the clips 462, thus providing a dual-action installation and removal mechanism. In the depicted embodiment, the hub 430 and coupling elements 460 are coaxially positioned within a cylindrically shaped outer body 420, for example, which is generally similar to the body 20 of FIGS. 1-6. As previously described above with respect to the coupling 10, at least one connecting member or transverse flange 450 is provided for retaining the hub 430 concentrically or coaxially within the outer cylindrical housing 420 of the coupling 400. As such, one or more vents 454 can be provided as desired.

In alternative example forms, the female connector FC of each syringe S can be installed with the coupling 400 by pushing (without twisting) due to the snap connection provided by the split collar and the rib R (e.g., flexibility of the clips 462), but is generally prevented from being pulled therefrom, for example, unless the syringe S or coupling 400 is generally rotated relative to the other. Optionally, attachment can be provided by twisting on and off due to the thread 464 on the clips 462, for example, whereby engagement of the rib R of the female connector FC with the threads 464 provide axial movement therebetween for attachment or detachment from the female connector FC. Preferably, in some example embodiments, the allowable flexibility of the clips 462 can be adjusted such that attachment and detachment (pushing, pulling, twisting) of the syringe S and coupling 400 can be configured as desired.

According to one example form, the clips 462 preferably provide the user with tactile feedback during attachment (and/or detachment) of the coupling 400 to/from the syringe S. For example, according to some example forms, the flexibility of the clips during interengagement with the female connector FC of the syringe S causes the clips to snap back into place, for example, after being flexed outwardly due to engagement with the ribs R of the female connector FC. Thus, according to example forms of the invention, the coupling 400 can preferably provide the user with an indication that the coupling is generally securely coupled with the female connector FC. Optionally, after the clips provide the tactile feedback (e.g., indicating engagement therebetween), the user may further twist the coupling 400 relative to the female connector FC to ensure the connection therebetween is substantially snug and secure.

According to example embodiments, the male tips 432 of the hub 430 can be sized and shaped at least partially different from the male tips 32, 132, and 232 as described above. For example, as the coupling elements 460 (e.g., clips 462) interengage a portion of the female connector FC, the male tips 432 (and the outer peripheral shape of the hub 430) are not entirely relying on a frictional fit with the female connector FC to remain engaged therewith. Rather, since the threads 464 of the clips 462 are engaged with the ribs R of the female connector FC, the male tips 432 and outer periphery portions of the hub 430 can be shaped as desired. According to one example form, the male tips 432 comprise a surface or chamfered edge 433, which is generally at least partially smaller with respect to the chamfered edge 333. Optionally, the chamfered edge 433 can be shaped as desired.

Figure 16:
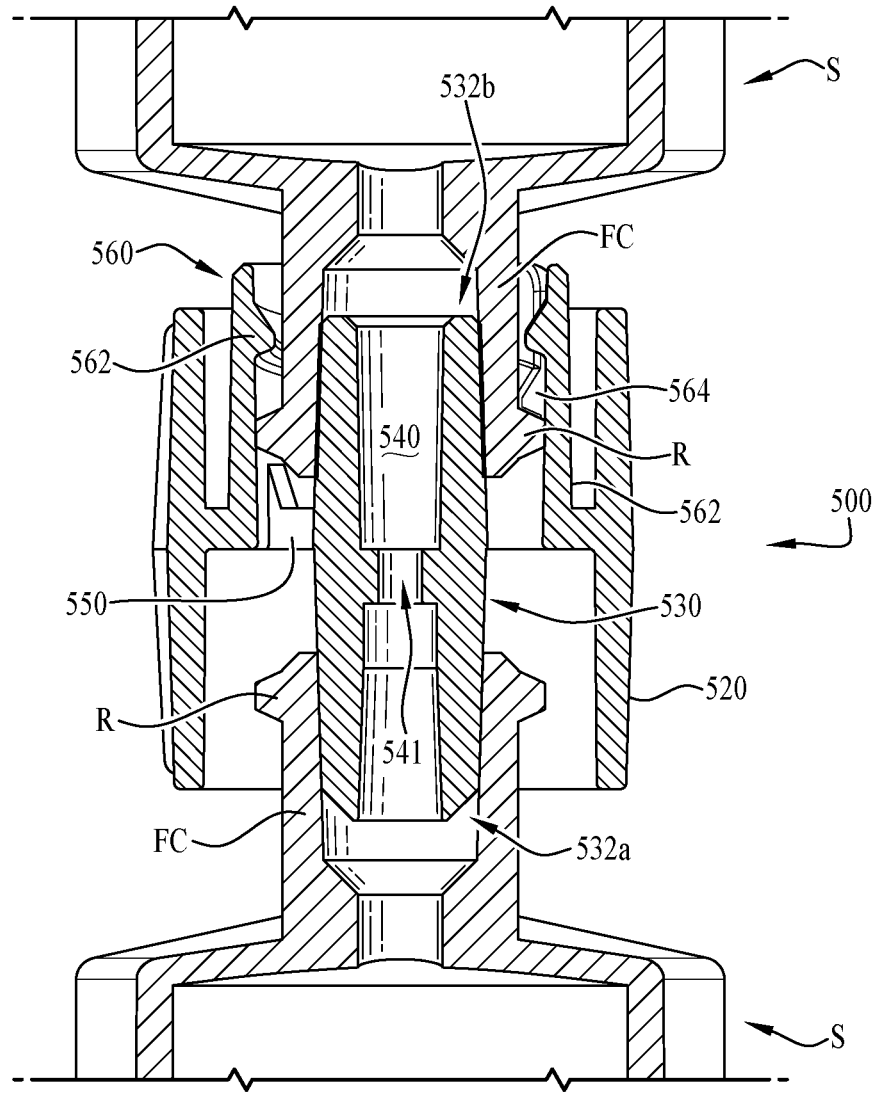
FIG. 16 is a detailed cross-sectional view of a syringe-to-syringe coupler coupled between two syringes according to another example embodiment of the present invention.
Figure 17:
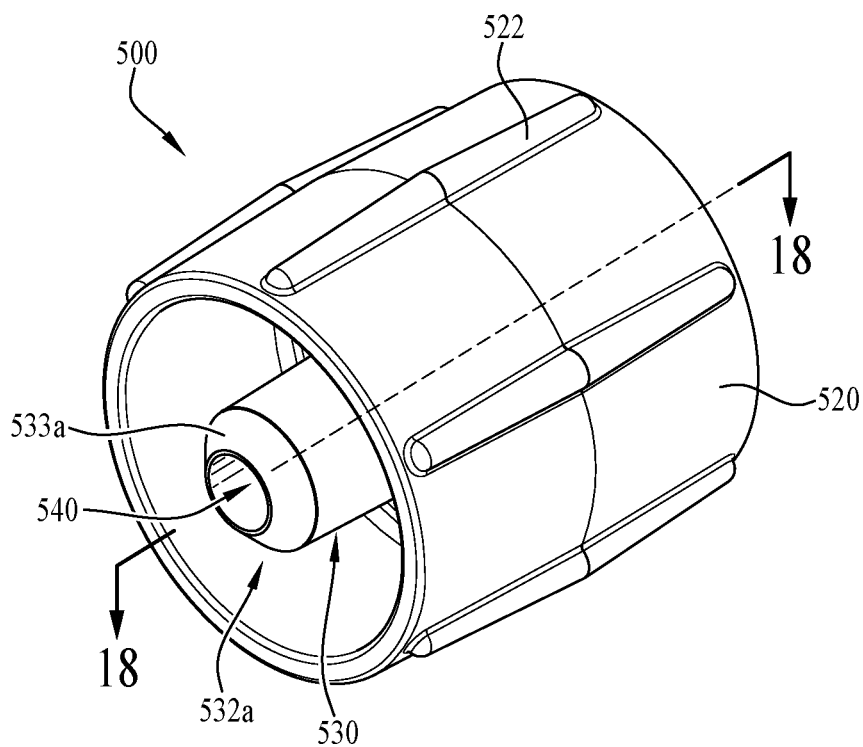
FIG. 17 shows a perspective view of the syringe-to-syringe coupler of FIG. 16.
Figure 18:
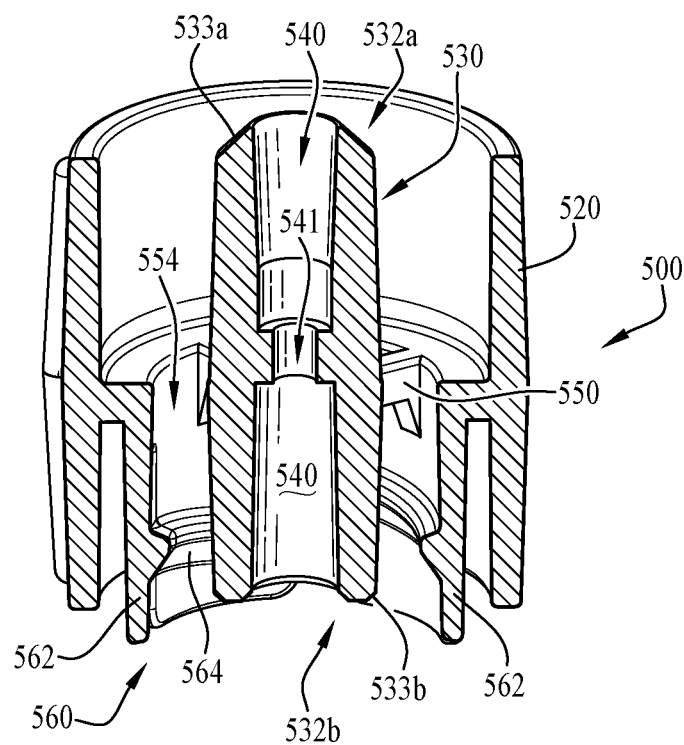
FIG. 18 shows a sectional view of the syringe-to-syringe coupler of FIG. 17 taken along line 18-18.

FIGS. 16-18 show a syringe-to-syringe coupler 500 according to another example embodiment of the present invention. The coupler 500 is configured to removably engage a first syringe S with a slip-fit coupling and a second syringe with a threaded coupling. In example embodiments, the coupler 500 includes a hub 530, fluid conduit 540 and outer body 520 of similar size and shape as the previously described embodiment. In example embodiments, a neck or ring is provided within the conduit 540, which can further reduce the volume of the conduit, for example, by providing a generally smaller intermediate conduit portion 541, which is generally positioned at a midpoint of the conduit 540. In example embodiments, one of the ends of the hub comprises a first male tip 532a (e.g., configured for a slip-fit connection) and the other end of the hub 530 comprises a second male tip 532b (e.g., similar to the male tips 432 of coupling 400).

The coupler 500 also includes an engagement member or coupling element 560 comprising a plurality of clips 562, for example, as depicted in the coupling 400. Similarly, at least one of the clips 562 comprises a rib or thread 564 formed on an interior portion thereof for providing interengagement with one or more of the ribs R of the female connector FC. In a similar fashion with respect to the coupling 400, the coupling element 560 is configured to be coupled to the female connector FC of the syringe S by configuring the one or more ribs R of the female connector FC to interengage with the threads 564 of the outer housing 562, for example, by rotation of one of the syringe or the coupling 500 relative to the other, or by axially moving one of the coupling 560 or female connector FC toward the other to cause the clips 562 to flex outwardly to cause a snap-fit, tactile connection with the female connector FC. The second syringe S is slip fitted onto the second male tip 532a. As similarly described above, the coupling 500 comprises at least one connecting member or transverse flange 550 for retaining the hub 530 concentrically or coaxially within the outer cylindrical housing 520 of the coupling 500. Furthermore, one or more vents 554 can be provided. In the depicted example embodiment, four transverse flanges 550 and four vents 554 are provided.

Figure 19:
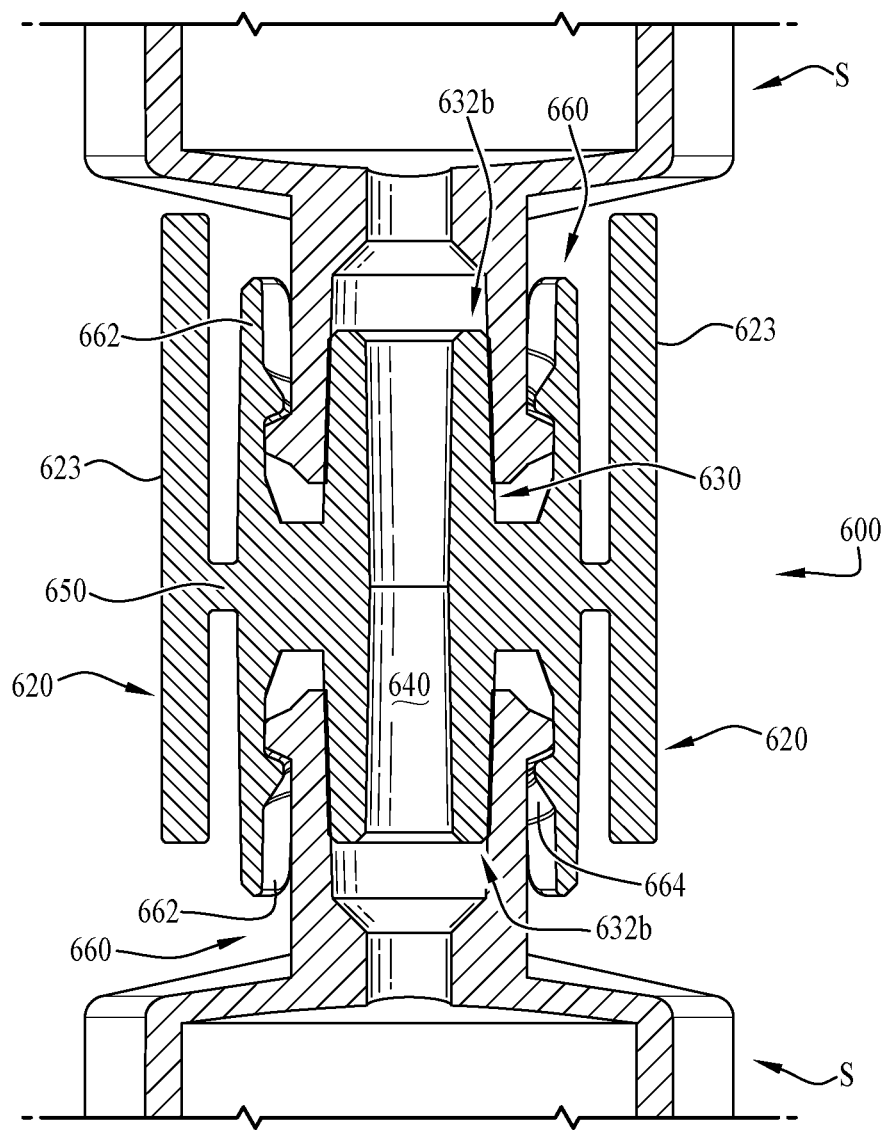
FIG. 19 is a detailed cross-sectional view of a syringe-to-syringe coupler coupled between two syringes according to another example embodiment of the present invention.
Figure 20:
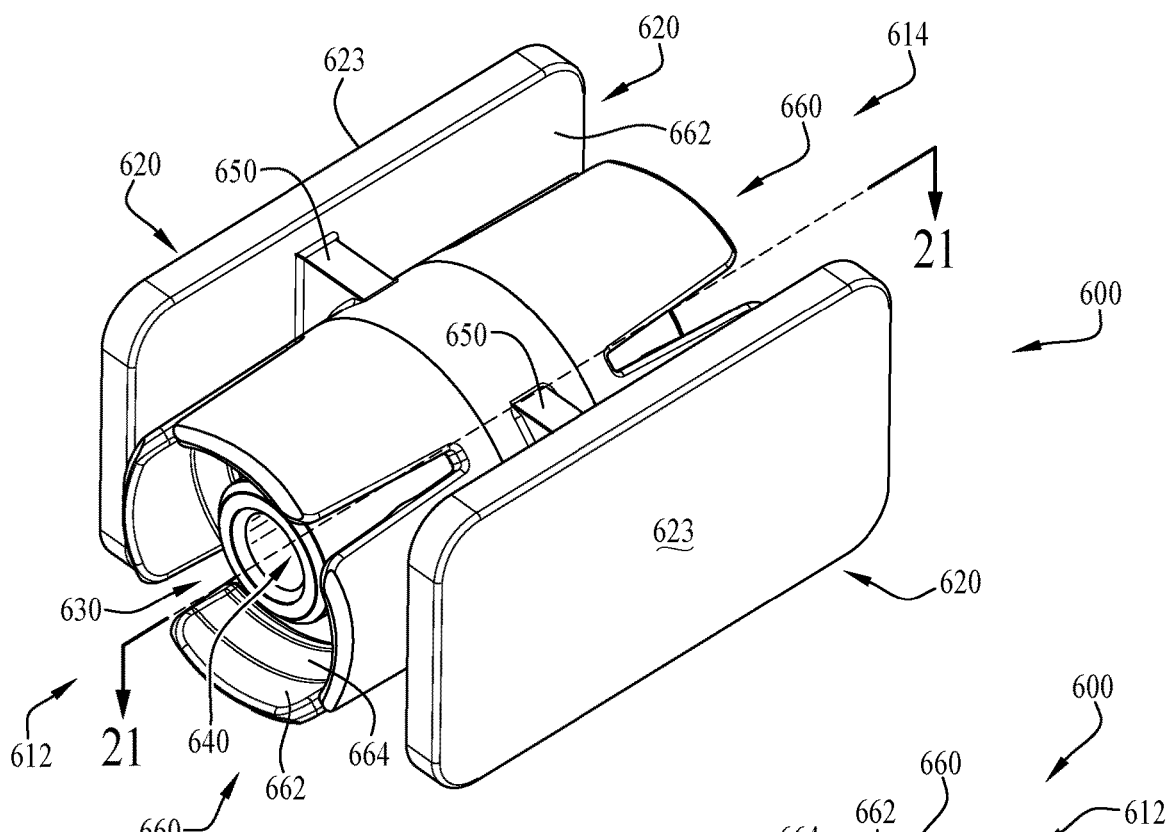
FIG. 20 shows a perspective view of the syringe-to-syringe coupler of FIG. 19.
Figure 21:
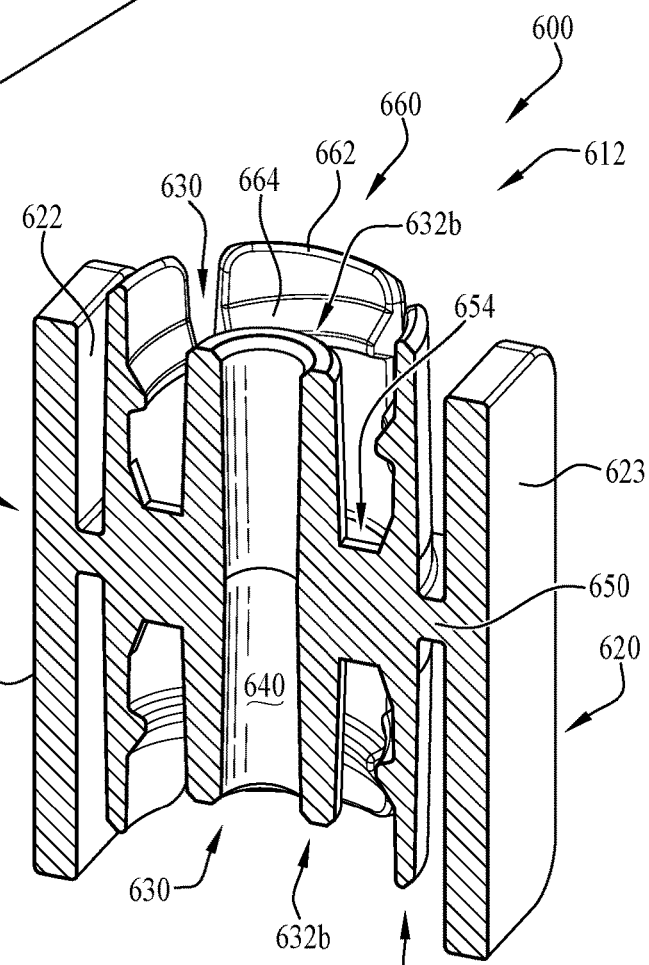
FIG. 21 shows a sectional view of the syringe-to-syringe coupler of FIG. 20 taken along line 21-21.

FIGS. 19-21 show a syringe-to-syringe coupler 600 according to another example embodiment of the present invention. The coupler 600 is configured to removably engage two syringes S with threaded couplings. The coupler includes a hub 630 and fluid conduit 640 of similar size and shape as the previously described embodiment. The coupler also includes two coupling elements 660 comprising four clips 662 with threaded portions 664 similar to previously described couplers 400. In the depicted embodiment, the coupler 600 further includes two generally oppositely-positioned and outwardly offset planar members or gripping panels 620 attached to the outer surface of the coupling elements 660. The panels 620 are oriented on opposite sides of the cylindrical coupling elements such that the inner face of the panel 622 is oriented toward the length of the hub 630, for example such that the elongate extension of each of the panels 620 is generally oriented parallel with the extension of the hub 630. In example embodiments, an exterior or outer surface 623 of one or both of the panels 620 can comprise one or more openings, indentations, recesses, protrusions or other texturizing or grip-enhancing surface features to provide a gripping surface for a user that is grasping the coupling 600, for example, by placement of one or more fingers against the outer surface 623 generally providing a squeezing-like action with two or more fingers.

In the depicted example embodiment, the panels are offset with respect to the length or extension of the hub 630, for example, such that the length of the panel 620 is not centered with the length of the hub 630, and thus causing one of the coupling elements 660 to extend beyond the end of the ends of the panels 420, for example, at a first end 412 of the coupler 400, and wherein another of the coupling elements 660 is generally positioned to be at least partially recessed below the ends of the panels 620 as is shown at the second end 614.

In alternate example embodiments, the panels 620 can be positioned and oriented as desired with respect to the hub 630. Accordingly, according to example embodiments, the coupling 600 is generally similar to the coupling 400 as described above, for example, wherein the hubs 430, 630, the fluid conduits 440, 640, and the transverse flanges 450, 650 are substantially similar in size and functionality, and wherein the cylindrical outer body 620 is generally replaced with the oppositely-positioned and outwardly offset planar members 620 to define the coupling 600. According to some example forms, one or more openings (or openings extending entirely through the panels 620) can be provided within one or more portions of the planar members 620 as desired, for example, which can be shaped and sized as desired.

As will be described in the embodiments below, the hubs, fluid conduits and transverse flanges (and optional vents) generally remain similar to at least one of the embodiments as described above, or for example, such that an end (or one of the male tips) of the embodiments as described above is generally similar in size, shape and functionality. Furthermore, the panels 620 (and 720, 820, 920, 1020, 1120, 1220, and 1320, respectively) are generally similarly oppositely-positioned and outwardly offset with respect to the fluid conduit 640 (and 740, 840, 940, 1040, 1140, 1240 and 1340, respectively).

Figure 22:
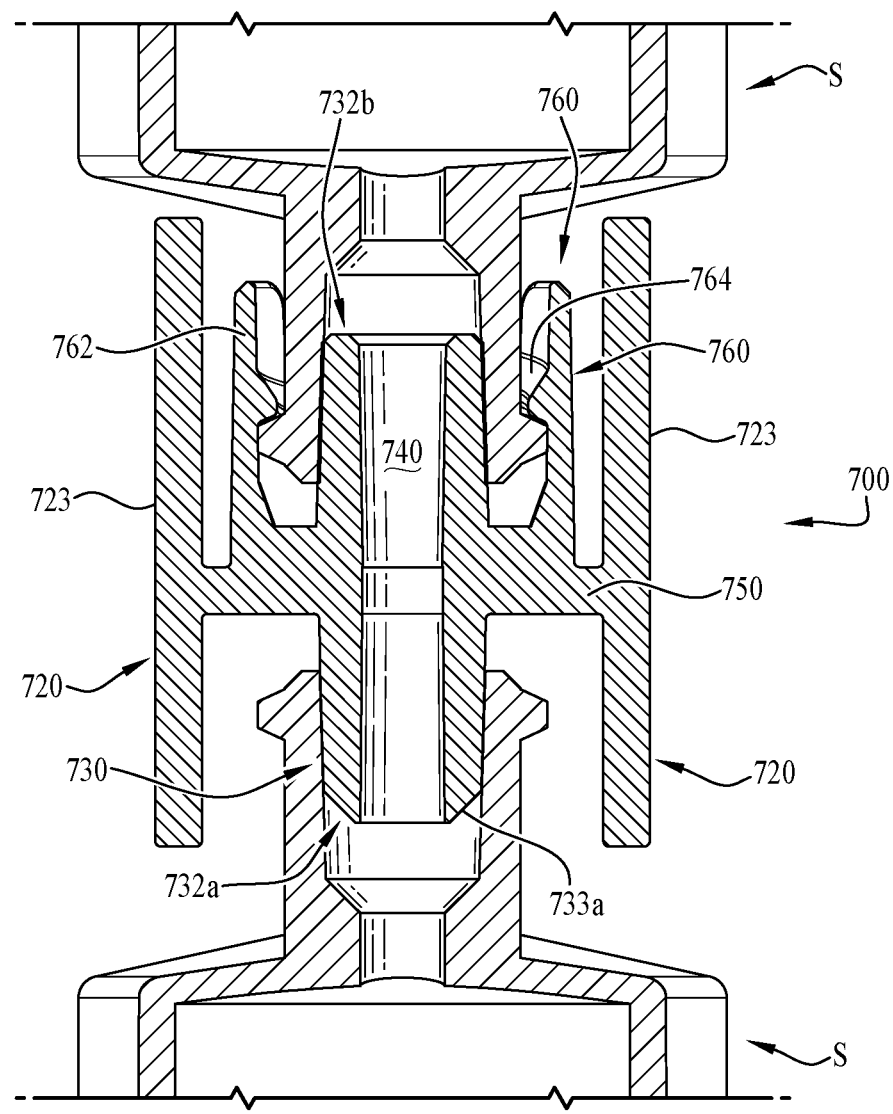
FIG. 22 is a detailed cross-sectional view of a syringe-to-syringe coupler coupled between two syringes according to another example embodiment of the present invention.
Figure 23:
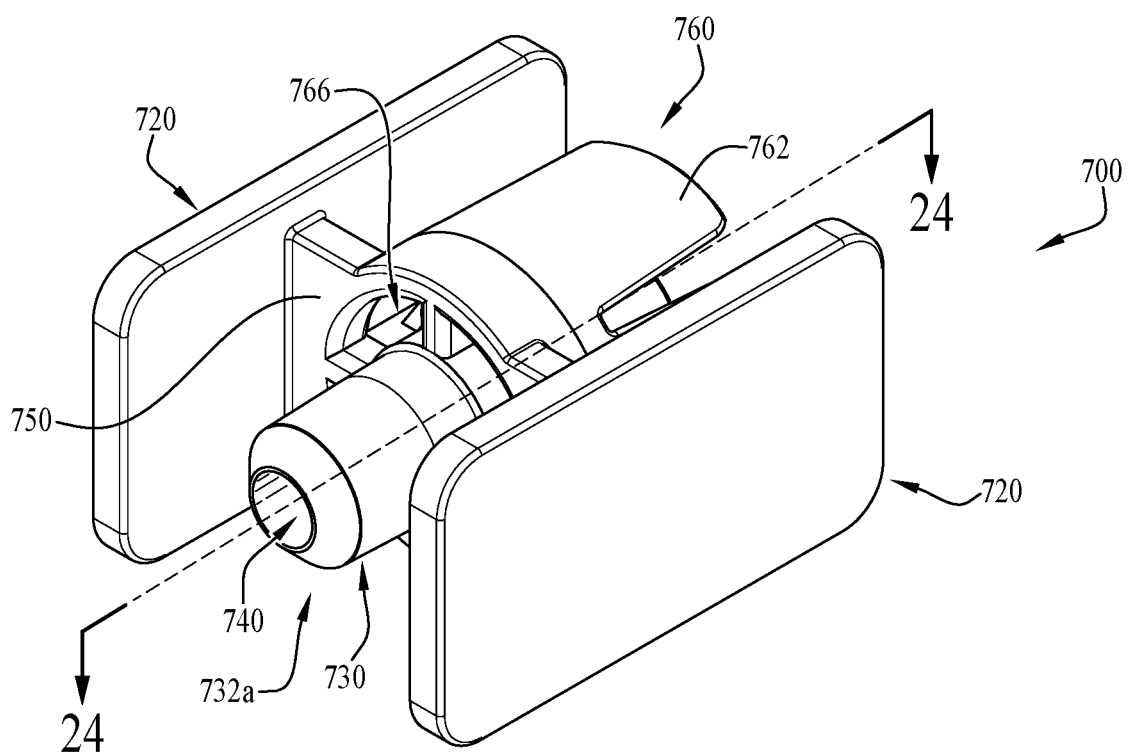
FIG. 23 shows a perspective view of the syringe-to-syringe coupler of FIG. 22.
Figure 24:
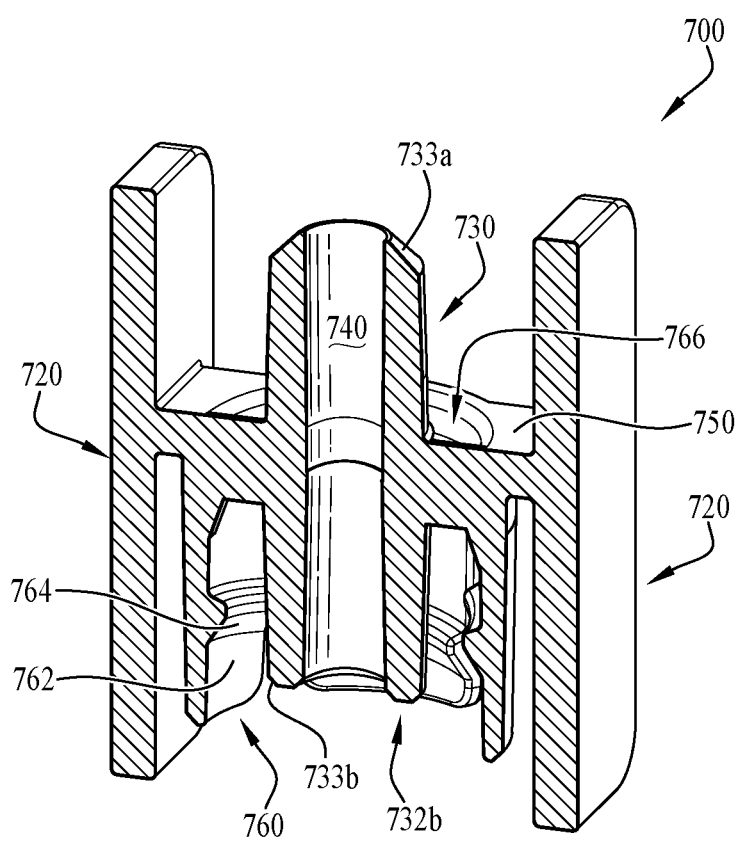
FIG. 24 shows a sectional view of the syringe-to-syringe coupler of FIG. 23 taken along line 24-24.

FIGS. 22-24 show a syringe-to-syringe coupler 700 according to another example embodiment of the present invention. The coupler 700 is configured to removably engage a first syringe S with a slip-fit coupling and a second syringe with a threaded coupling 760. The coupler 700 includes a hub 730 and fluid conduit 740 of similar size and shape as the previously described embodiment. The coupler 700 includes a plurality of clips 762 760 comprising one or more clips 762 with threaded portions 764 and two gripping panels 720 similar to those described in the previous embodiment. In the depicted embodiment, the coupler 700 further includes a plurality of vents 766 positioned at the bottom of the coupling element 760.

Figure 25:
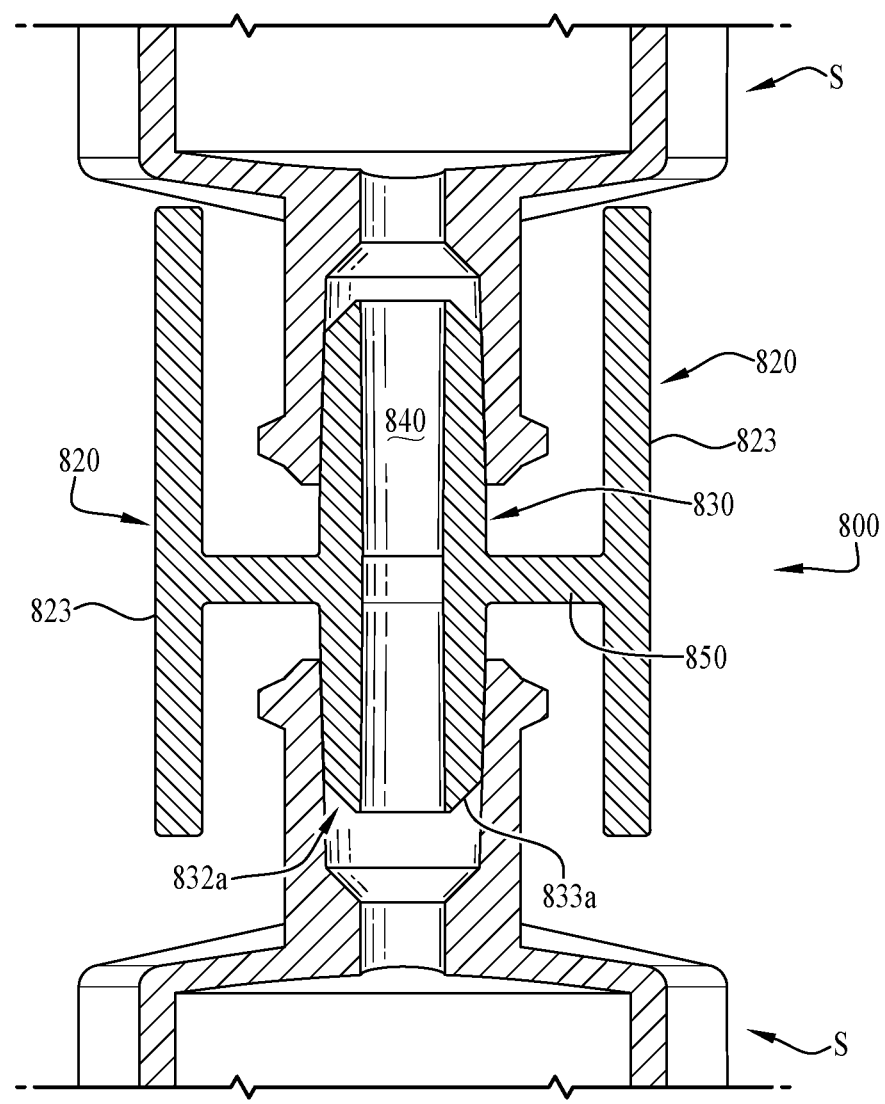
FIG. 25 is a detailed cross-sectional view of a syringe-to-syringe coupler coupled between two syringes according to another example embodiment of the present invention.
Figure 26:
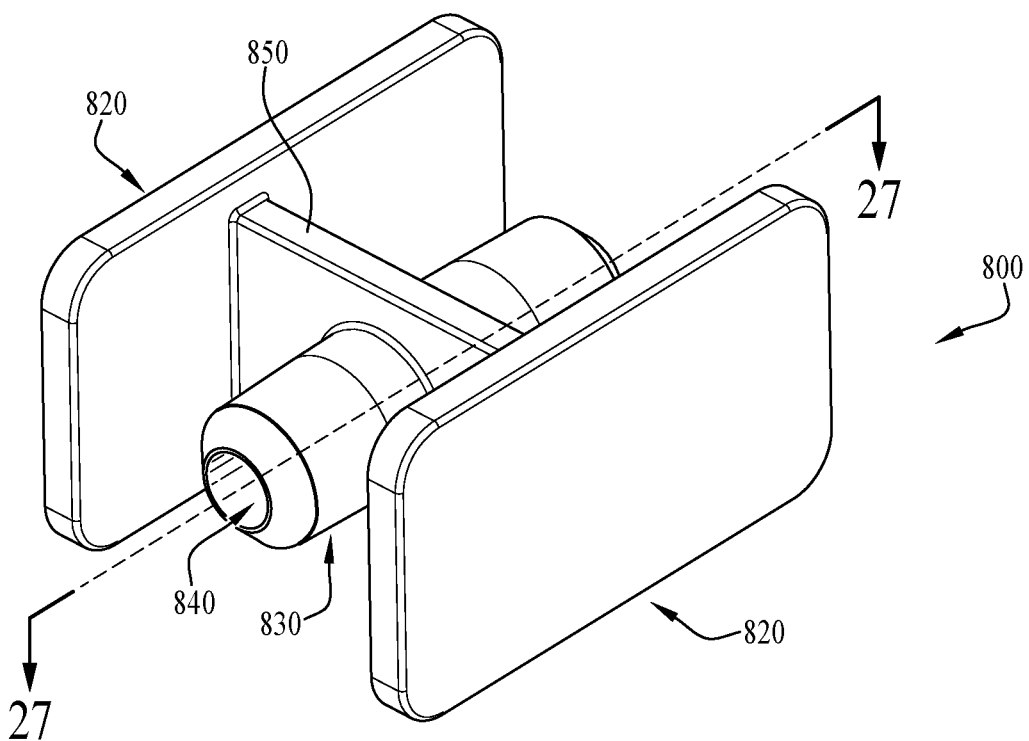
FIG. 26 shows a perspective view of the syringe-to-syringe coupler of FIG. 25.
Figure 27:
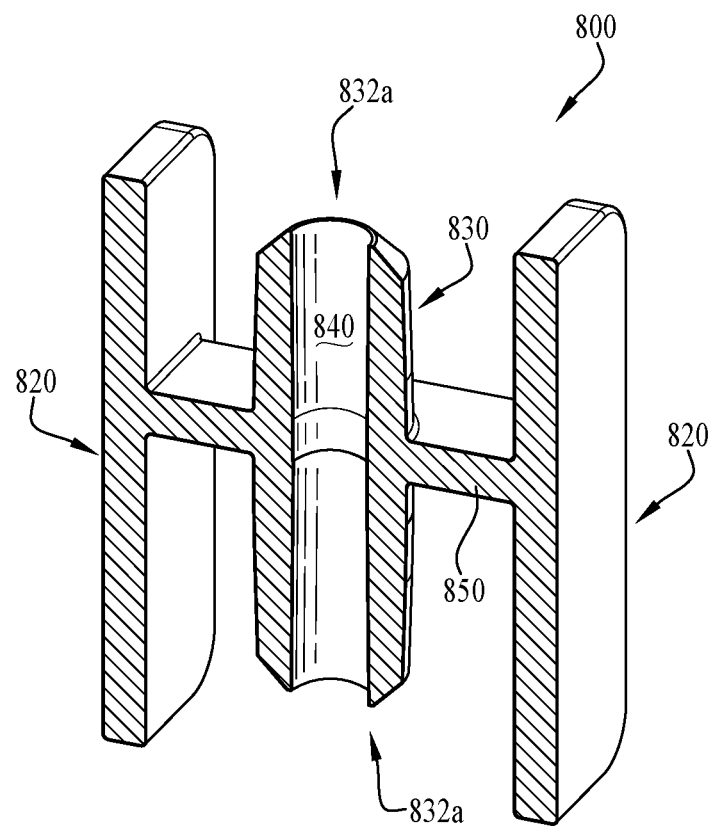
FIG. 27 shows a sectional view of the syringe-to-syringe coupler of FIG. 26 taken along line 27-27.

FIGS. 25-27 show a syringe-to-syringe coupler 800 according to another example embodiment of the present invention. The coupler 800 is configured to engage two syringes S with a removable slip-fit coupling. The coupler 800 includes a hub 830 and fluid conduit 840 of similar size and shape as the previously described embodiment. The coupler 800 also includes two gripping panels 820 similar in size and shape to those described above. The gripping panels are attached to a flange 850 extending from a central portion of the hub 830.

Figure 28:
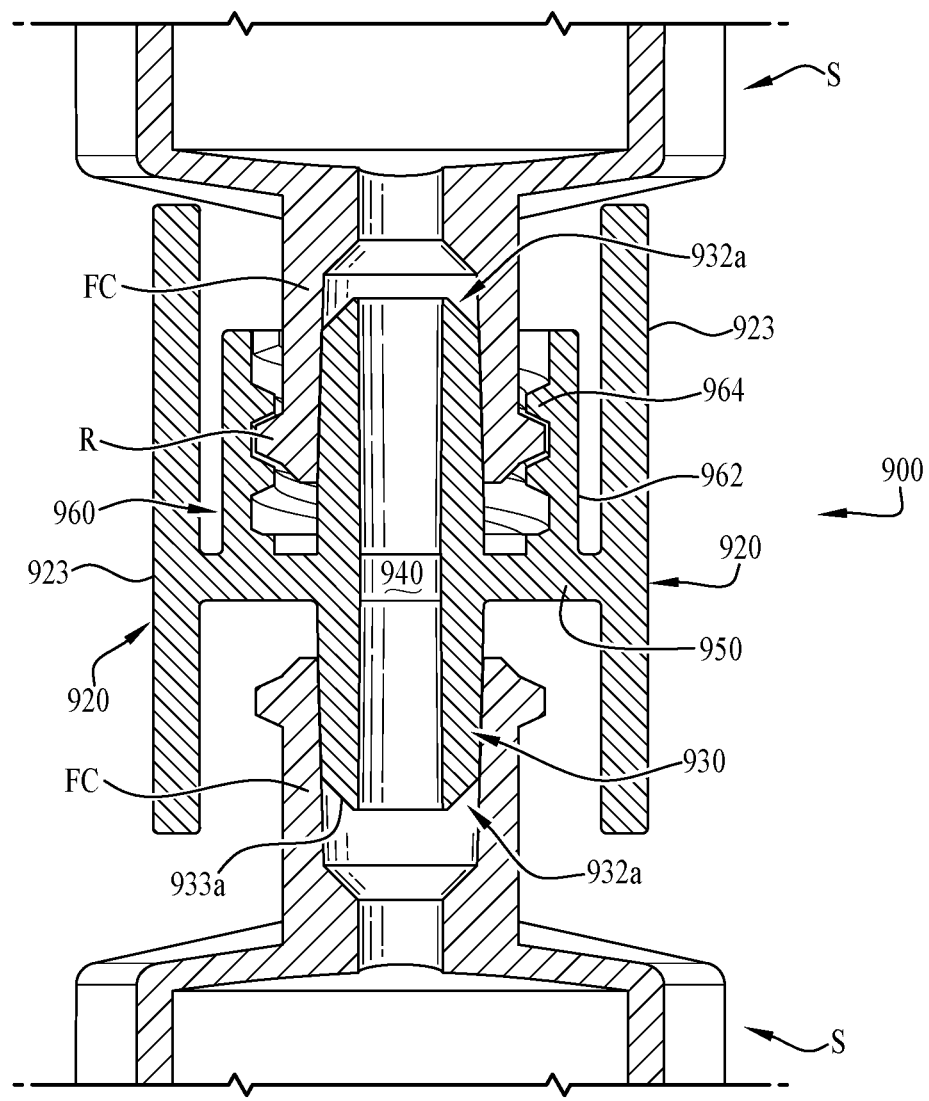
FIG. 28 is a detailed cross-sectional view of a syringe-to-syringe coupler coupled between two syringes according to another example embodiment of the present invention.
Figure 29:
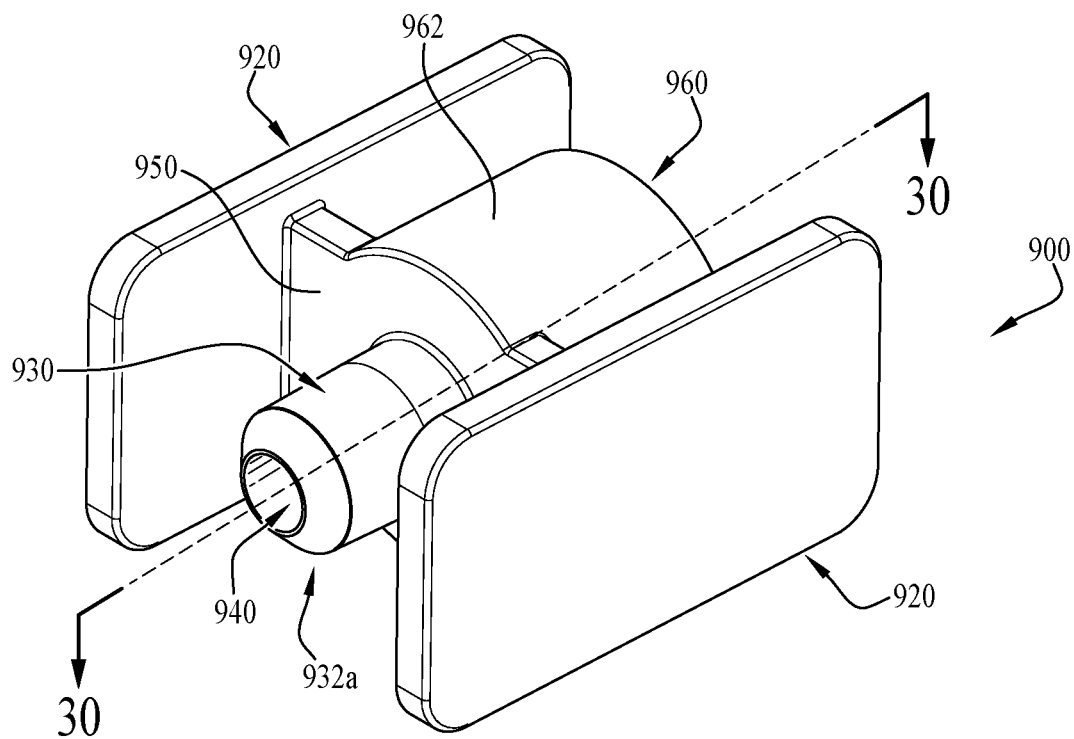
FIG. 29 shows a perspective view of the syringe-to-syringe coupler of FIG. 28.
Figure 30:
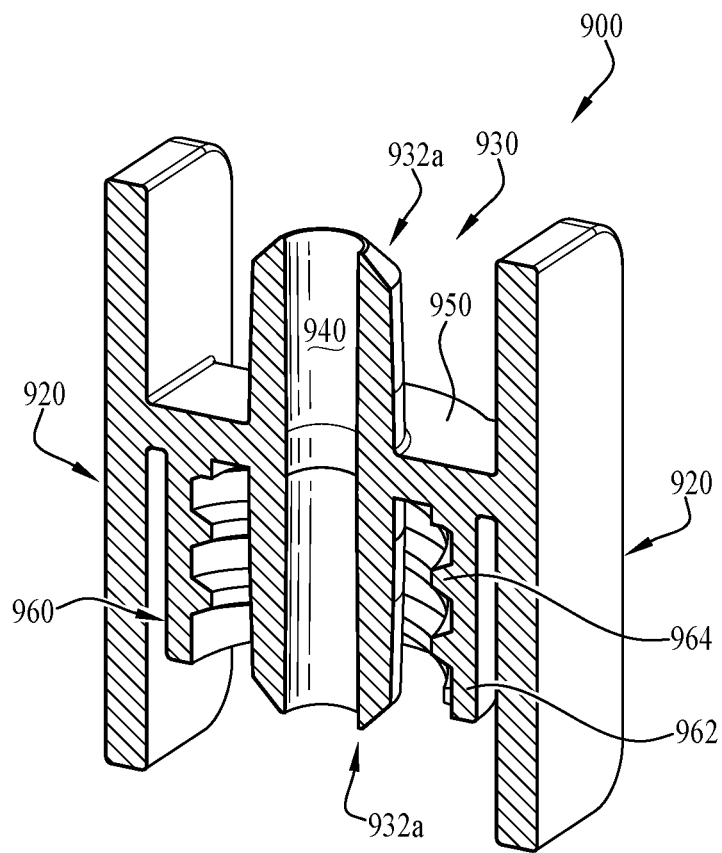
FIG. 30 shows a sectional view of the syringe-to-syringe coupler of FIG. 29 taken along line 30-30.

FIGS. 28-30 show a syringe-to-syringe coupler 900 according to another example embodiment of the present invention. The coupler 900 is configured to removably engage a first syringe S with a slip-fit coupling and a second syringe with a threaded coupling. The coupler 900 includes a hub 930, fluid conduit 940, flange 950 and gripping panels 920 of similar size and shape as the previous embodiment. The coupler 900 also includes a single coupling element 960. The coupling element 960 includes a generally cylindrically shaped outer collar member or outer housing 962 surrounding a male tip 932 such that the inner sidewall of the outer housing is generally coaxially arranged with the male tip thereby forming an annular space therebetween. The inner sidewall of the outer housing 962 includes screw threads 964. To removably engage a syringe S with the respective coupling element 260 the female connector FC is inserted into the annular space between the male tip 932a and the outer housing 962 such that the ribs are generally oriented to interengage with the threads 964 on the outer housing. The second syringe S is slip fitted onto the second male tip 932a.

Figure 31:
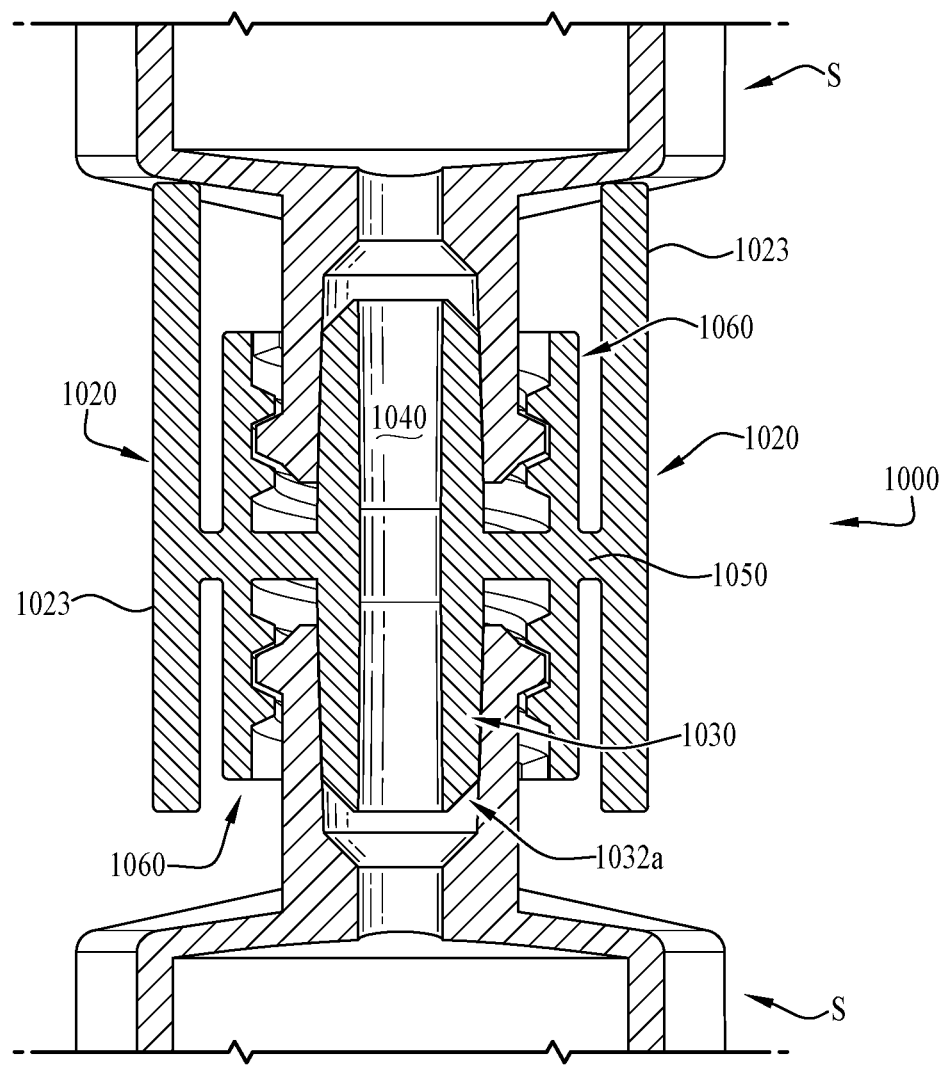
FIG. 31 is a detailed cross-sectional view of a syringe-to-syringe coupler coupled between two syringes according to another example embodiment of the present invention.
Figure 32:
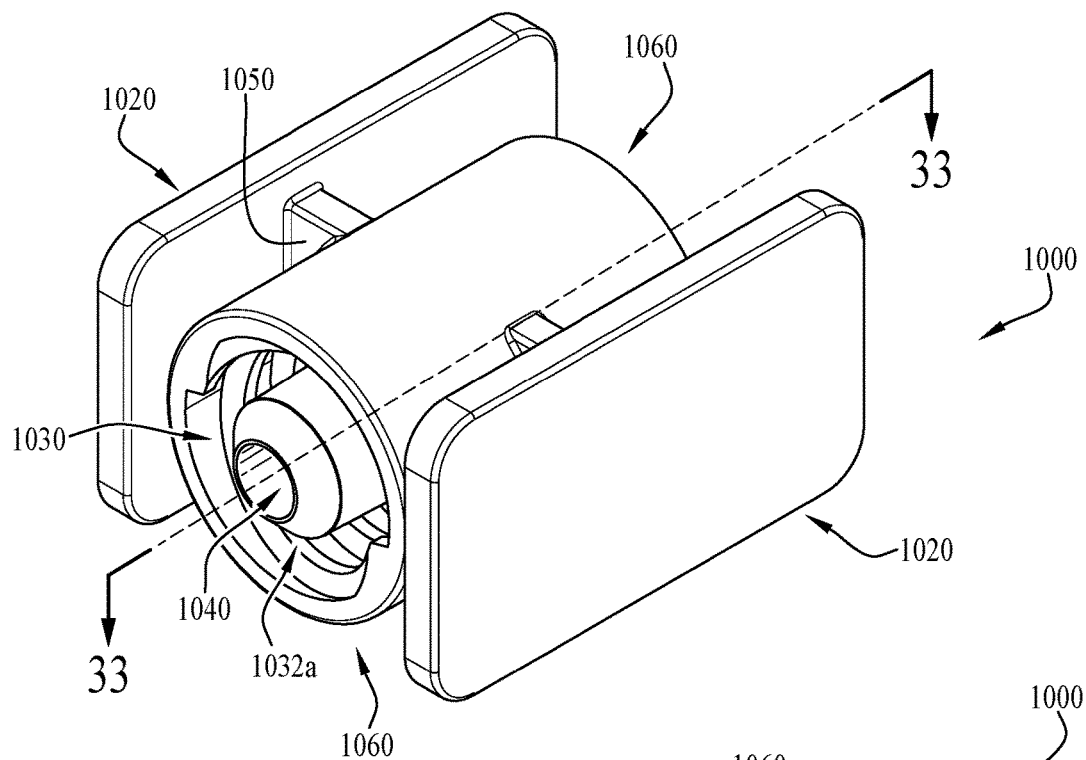
FIG. 32 shows a perspective view of the syringe-to-syringe coupler of FIG. 31.
Figure 33:
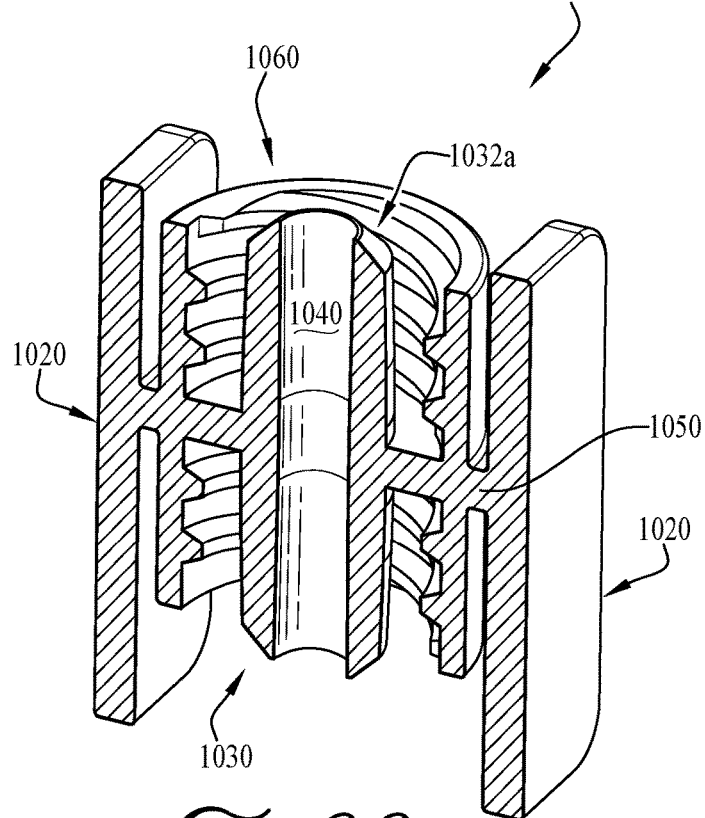
FIG. 33 shows a sectional view of the syringe-to-syringe coupler of FIG. 32 taken along line 33-33.

FIGS. 31-33 show a syringe-to-syringe coupler 1000 according to another example embodiment of the present invention. The coupler 1000 is configured to removably engage two syringes S with threaded couplings. The coupler 1000 includes a hub 1030, fluid conduit 1040, flange 1050 and gripping panels 1020 of similar size and shape as the previous embodiment. The coupler 1000 also includes two threaded coupling elements 1060 of similar size and shape of the coupling element in the previous embodiment. Each coupling element 1060 extends from the centrally positioned flange toward each respective male tip 1032.

Figure 34:
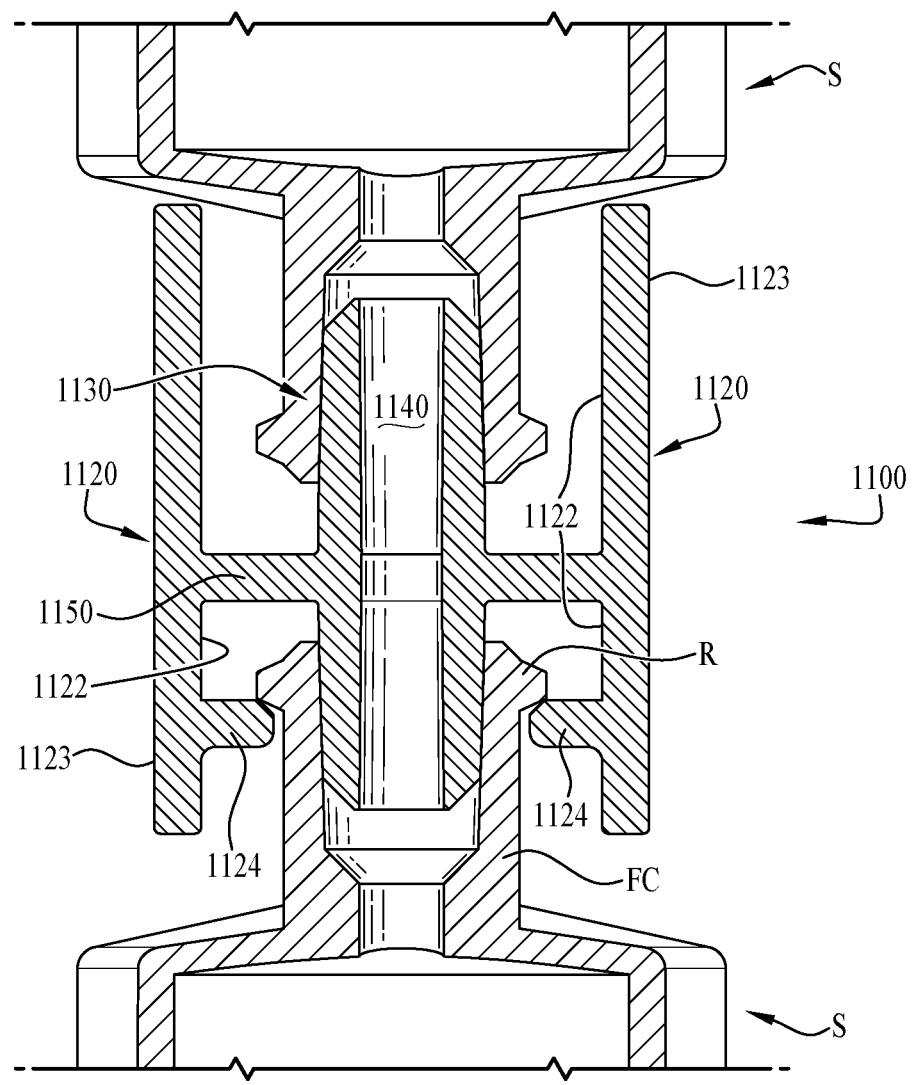
FIG. 34 is a detailed cross-sectional view of a syringe-to-syringe coupler coupled between two syringes according to another example embodiment of the present invention.
Figure 35:
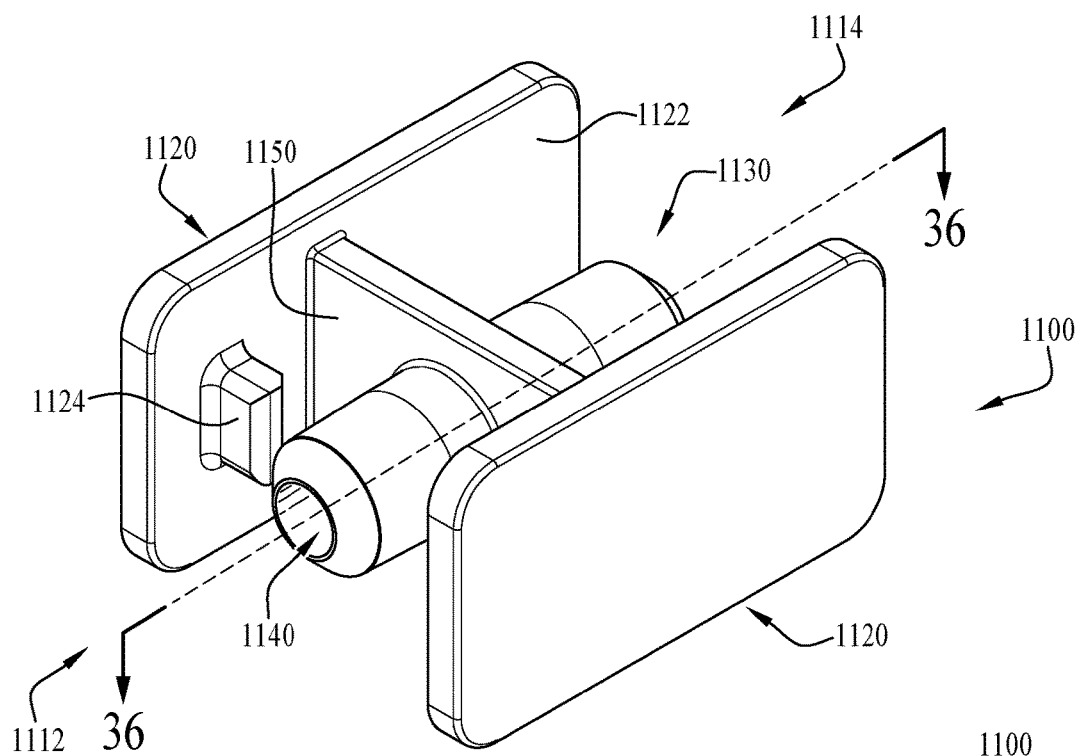
FIG. 35 shows a perspective view of the syringe-to-syringe coupler of FIG. 34.
Figure 36:
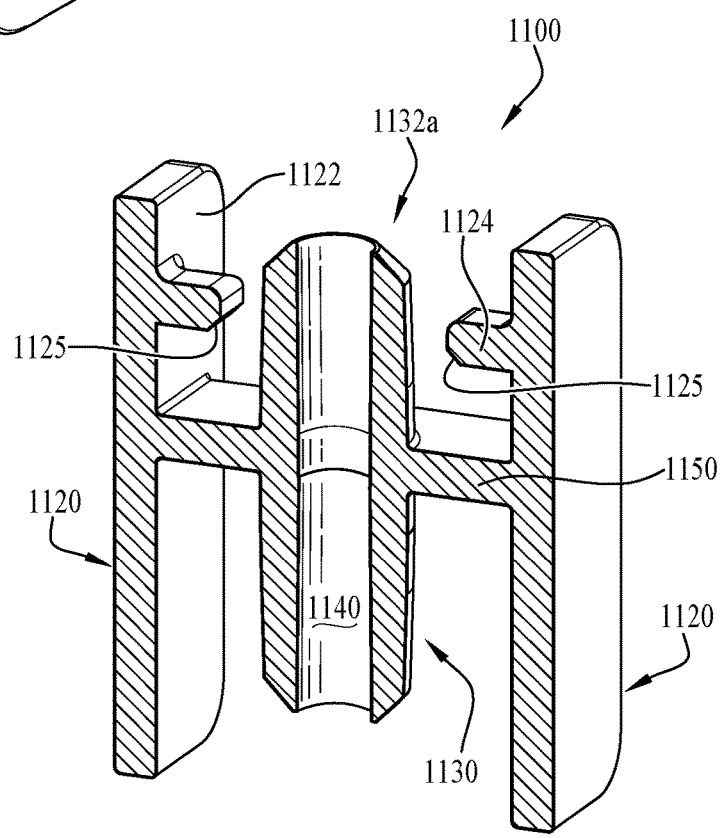
FIG. 36 shows a sectional view of the syringe-to-syringe coupler of FIG. 35 taken along line 36-36.

FIGS. 34-36 show a syringe-to-syringe coupler 1100 according to another example embodiment of the present invention. The coupler 1100 is configured to removably engage a first syringe S with a slip-fit coupling and permanently engage a second syringe S with a removable coupling. The coupler 1100 includes a hub 1130, fluid conduit 1140, flange 1150 and gripping panels 1120 of similar size and shape as the previous embodiment. The coupler 1100 further includes two fingers or extensions 1124 extending from the inner face 1122 of each of the panels 1120. In example embodiments, the extensions 1124 are configured for extending from the inner face 1122 (and generally at the same position with respect to each other) such that the rib R on the female connector FC of the syringe S can be removably engaged with an underside or angled surface 1125 of each of the extension 1124. Preferably, the surfaces 1125 can be angled as desired, for example, to provide for appropriate removable engagement with the extensions 1124.

According to one example embodiment, only one of the inner surfaces 1122 of the coupling 1100 may include the extension 1124, for example, such that it is only one of the ribs R of the female connector FC that is engaging the single extension.

Figure 37:
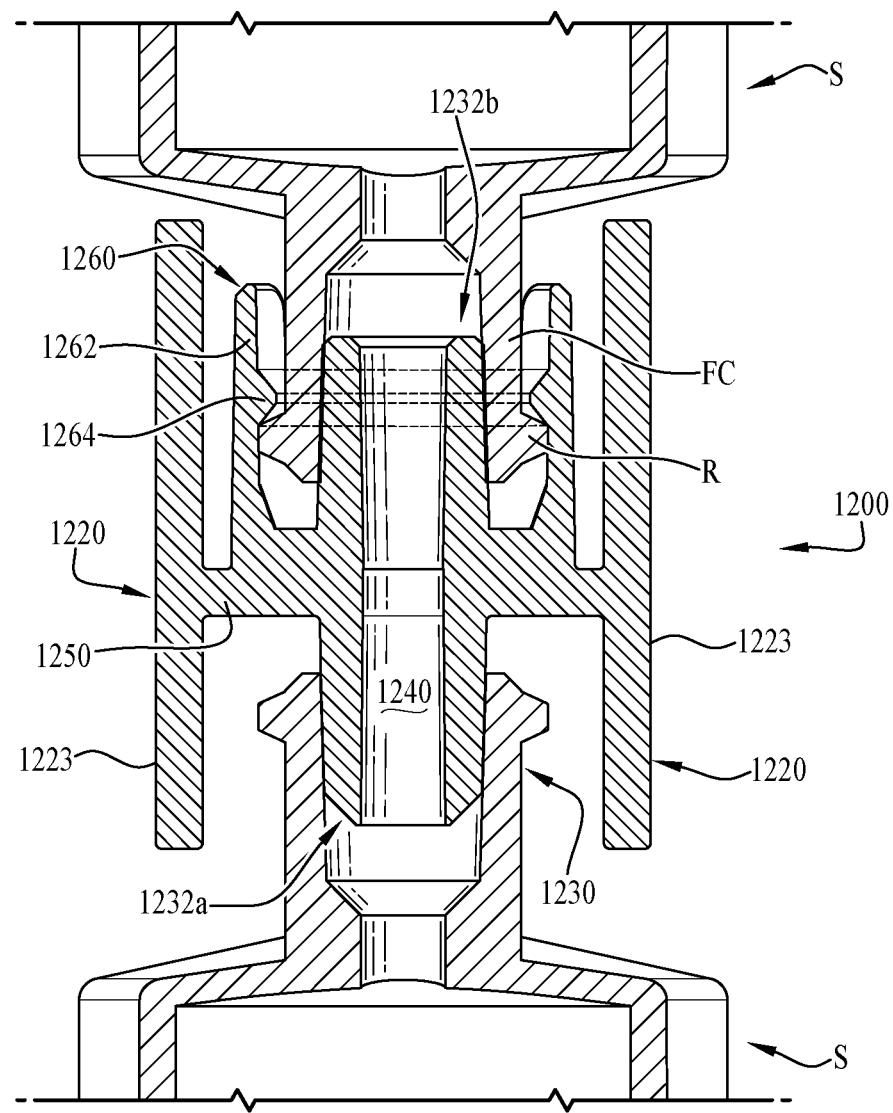
FIG. 37 is a detailed cross-sectional view of a syringe-to-syringe coupler coupled between two syringes according to another example embodiment of the present invention.
Figure 38:
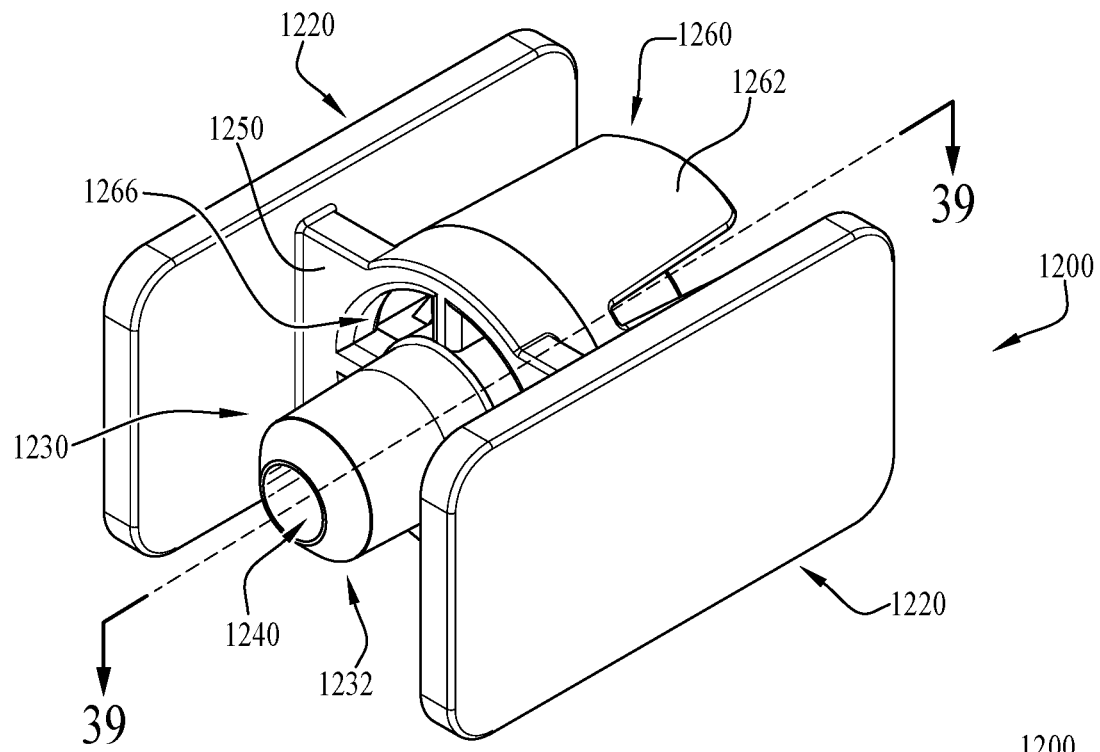
FIG. 38 shows a perspective view of the syringe-to-syringe coupler of FIG. 37.
Figure 39:
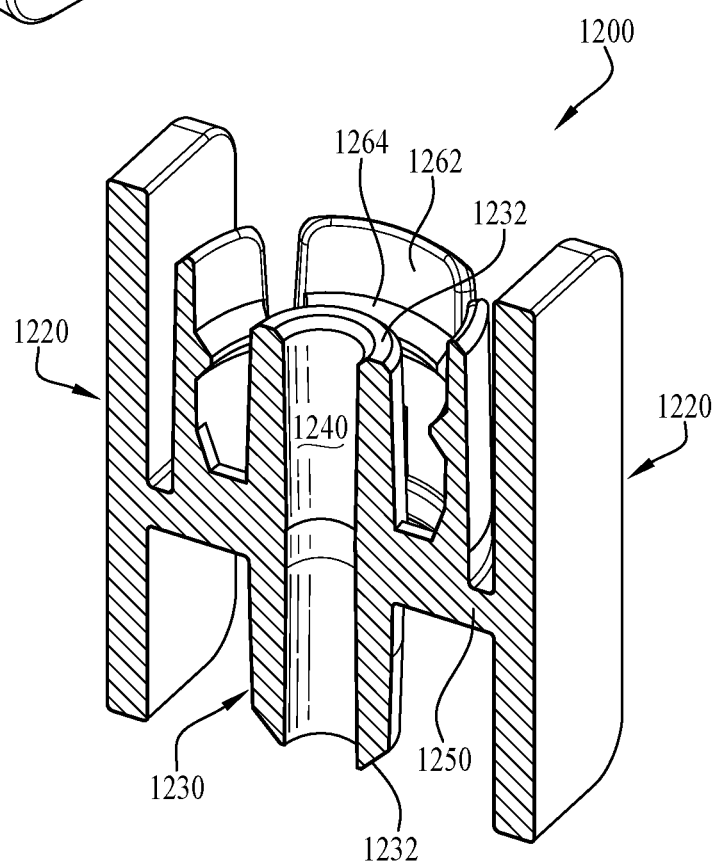
FIG. 39 shows a sectional view of the syringe-to-syringe coupler of FIG. 38 taken along line 39-39.

FIG. 37-39 show a syringe-to-syringe coupler 1200 according to another example embodiment of the present invention. The coupler 1200 is configured to removably engage a first syringe S with a slip-fit coupling and a second syringe S with a permanent coupling 1260. The coupler 1200 includes a hub 1230, fluid conduit 1240, flange 1250 and gripping panels 1220 of similar size and shape as the previous embodiment. The coupler 1200 includes the coupling element 1260, which generally functions substantially similar to the removable coupling elements comprising the four flexible clips. In example embodiments, the coupling element 1260 includes four tab members or clips 1262 extending from the central flange 1250 that generally form a circular array at a distance from the hub 1230 generally extending from the center of the hub toward one of the male tips 1232. An internal portion or wall of at least one of the clips 1262 includes rib 1264. In the depicted embodiment, each of the four clips 1262 includes a rib 1264, for example, which remains in a substantially similar horizontal plane around the inner surfaces of each of the clips 1262. In example forms, the female connector FC of each syringe S can be installed by pushing the snap connection provided by the split collar and the rib R. In example embodiments, the clips are configured to prevent the female connector FC of the syringe S from being removed from the coupling element 1262. In example embodiments, the coupler 1200 is permanently attached to the syringe S, for example, since rotation provides no axial movement as the rib 1264 is substantially horizontal. Furthermore, the flexibility of the clips 1262 are configured for little to no flexibility, for example, such that the permanent coupling 1260 provides for a one-way coupling action. In example embodiments, the clips 1262 are configured for flexing just enough for the ribs R of the female connector FC to pass around the rib 1264, but the clips 1262 remain substantially rigid without much flexture such that the female connector FC remains substantially permanently coupled with the permanent connector 1260. In the depicted embodiment, the coupler 1200 further includes in the flange 1250 at the base of the coupling element 1260, which can comprise one or more vents 1266 extending through a portion of the flange 1250.

Figure 40:
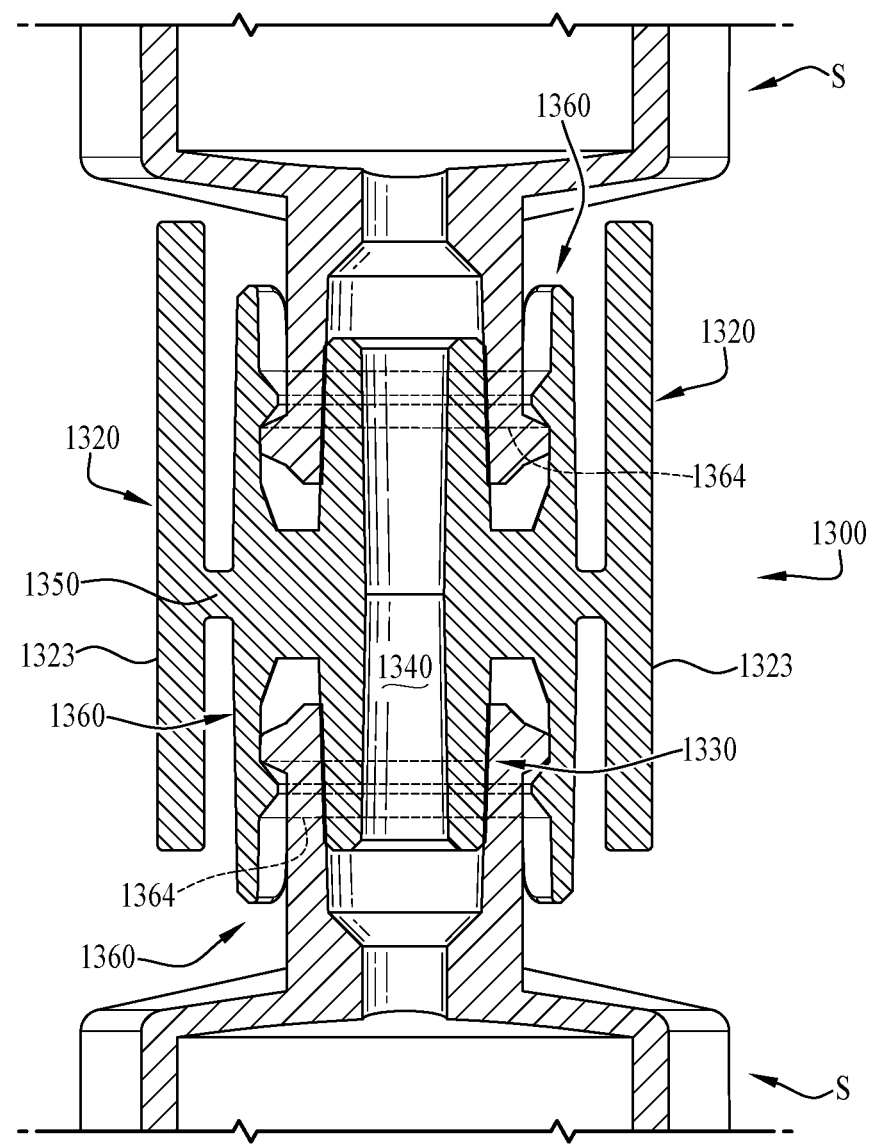
FIG. 40 is a detailed cross-sectional view of a syringe-to-syringe coupler coupled between two syringes according to another example embodiment of the present invention.
Figure 41:
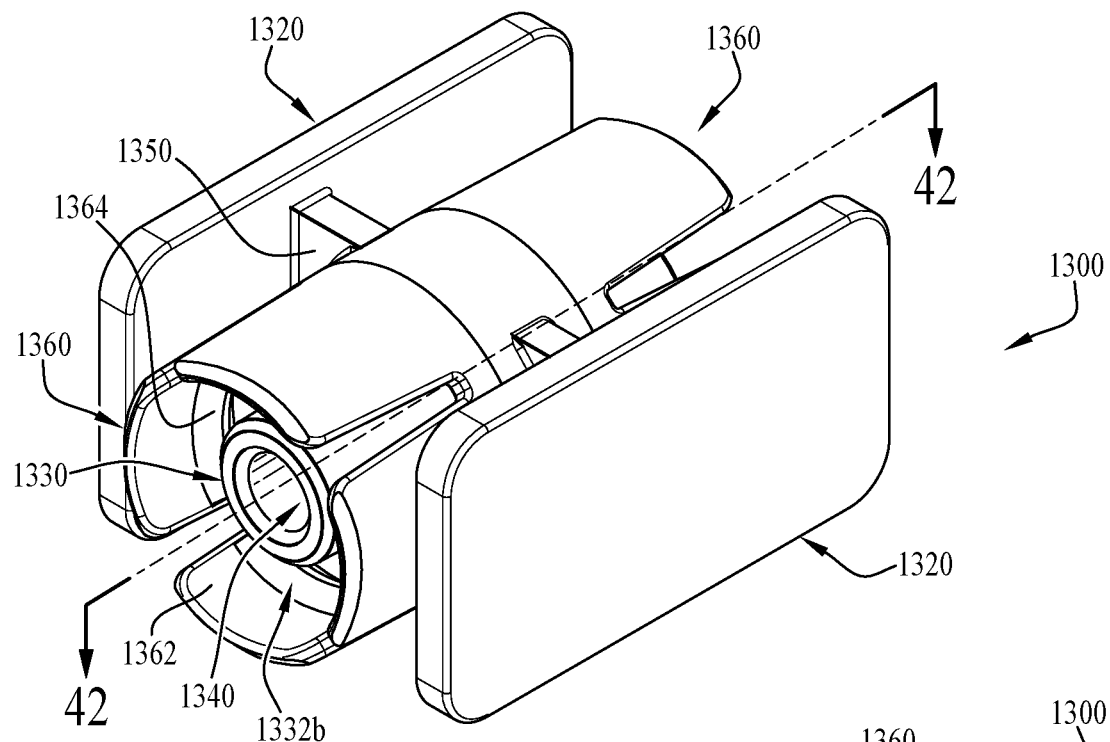
FIG. 41 shows a perspective view of the syringe-to-syringe coupler of FIG. 40.
Figure 42:
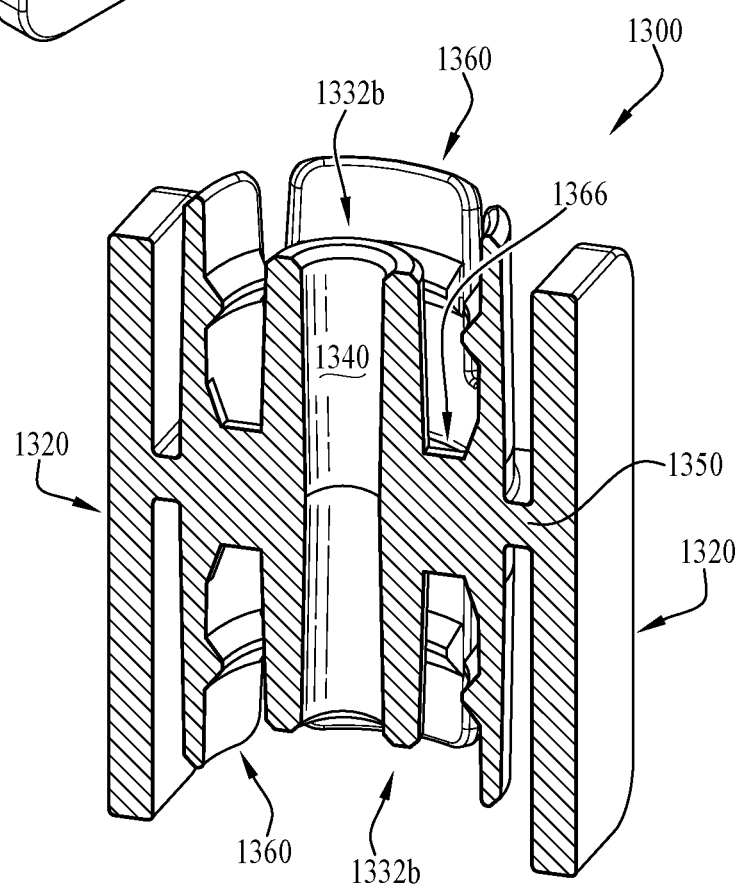
FIG. 42 shows a sectional view of the syringe-to-syringe coupler of FIG. 41 taken along line 42-42.

FIG. 40-42 show a syringe-to-syringe coupler 1300 according to another example embodiment of the present invention. The coupler 1300 is configured to removably engage two syringes S with threaded couplings. The coupler 1300 includes a hub 1330, fluid conduit 1240, flange 1350 and gripping panels 1320 of similar size and shape as the previous embodiment. The depicted embodiment includes two push fit coupling element 1360 similar to the previous embodiment.

According to another example embodiment of the present invention, one of the ends of the male tips (and thus a portion of the hub) can be configured for engagement with a syringe fill pump. In example embodiments, an end of the coupler can comprise a luer connector (e.g., luer lock or luer slip connector) for engagement with a tube set of the syringe fill pump, and the other end of the connector can be ENFit compatible for providing coupling engagement with an ENFit female connector FC. Optionally, the tube set of the syringe fill pump can be modified to connect with ENFit compatible connectors, and thus, any of the couplers as described herein are capable of coupling a syringe to a tube set of a syringe fill pump (e.g., via the coupler).

In example forms, the oral administration coupling is formed from a substantially rigid material (>700 MPA as per the ISO standard). Optionally, the coupling may be formed from a flexible, elastomeric material. In some example forms, the coupling can be formed from materials of one or more colors and/or may be at least partially translucent or clear, for example, such that the fluid or nutrients flowing therethrough are visible to the human eye. Optionally, the coupling can be in the formed from light protecting materials, for example, reflecting or blocking UV or other wavelengths to reduce or eliminate damage to contents by light.

According to additional example embodiments of the present invention, the coupling may be provided as an accessory to a bottle or variable-volume container, for example, as disclosed in U.S. patent application Ser. No. 13/191,721, which is incorporated herein by reference. As such, the coupling may be provided to facilitate transfer of fluids between the bottle and a syringe.

While the invention has been described with reference to preferred and example embodiments, it will be understood by those skilled in the art that a variety of modifications, additions and deletions are within the scope of the invention, as defined by the following claims.

What is claimed is:

1. A coupling for facilitating the transfer of fluids or medications, the coupling comprising:
   a centrally-positioned hub extending from a first end to a second end, each end of the hub comprising a male tip;
   a fluid delivery conduit provided within the hub and extending between the first and second ends; and
   a body outwardly offset from the hub;
   at least one connecting member connecting the hub with the body; and
   at least one engagement member for providing coupling engagement with a syringe, wherein the at least one engagement member extends from the at least one connecting member.

2. The coupling of claim 1, wherein at least one of the male tips comprise a male ENFit coupling.

3. The coupling of claim 1, wherein the at least one engagement member is configured for removable coupling engagement with the syringe.

4. The coupling of claim 1, wherein the at least one engagement member is configured for permanent coupling engagement with the syringe.

5. The coupling of claim 1, wherein one of the first or second ends of the hub is in the form of a luer connector for connection with a tube set of a syringe fill pump, and wherein the other of the ends is in the form of an ENfit connector for connection with an ENfit female connector of a syringe.

6. The coupling of claim 1, wherein the at least one engagement member comprises a clip having a rib extending from an internal surface thereof.

7. The coupling of claim 1, wherein the at least one engagement member comprises four clips.

8. The coupling of claim 7, wherein at least one of the four clips comprises a rib extending from an internal surface thereof.

9. The coupling of claim 8, wherein the rib extends along a helical path to provide for removable engagement with the one or more lugs of the female connector of at least one of the syringes.

10. The coupling of claim 8, wherein the rib extends along a horizontal path to provide for permanent engagement with the one or more lugs of the female connector of at least one of the syringes.

11. The coupling of claim 1, wherein the body comprises two generally planar members oppositely-positioned and outwardly offset from the hub.

12. The coupling of claim 11, wherein the planar members are generally rectangular in shape.

13. The coupling of claim 11, wherein the at least one engagement member extends from an internal surface of at least one of the planar members for providing engagement with the one or more lugs of a female connector of at least one of the syringes.

14. The coupling of claim 1, wherein the at least one engagement member comprises a collar member comprising threads formed on an internal portion thereof, and wherein the threads are configured for removable engagement with the one or more lugs of a female connector of at least one of the syringes.

* * * * *